(12) United States Patent
Dickman et al.

(10) Patent No.: US 8,415,328 B2
(45) Date of Patent: Apr. 9, 2013

(54) FACTOR VIIA INHIBITOR

(75) Inventors: Daniel A. Dickman, San Ramon, CA (US); Dange Vijay Kumar, Salt Lake City, UT (US); Colin O'Bryan, San Francisco, CA (US); Roopa Rai, San Carlos, CA (US); William Dvorak Shrader, Belmont, CA (US); Kieron Wesson, Burlingame, CA (US)

(73) Assignee: Pharmacyclics, Inc, Sunnyvale, CA (US)

( * ) Notice: Subject to any disclaimer, the term of this patent is extended or adjusted under 35 U.S.C. 154(b) by 0 days.

(21) Appl. No.: 13/100,058

(22) Filed: May 3, 2011

(65) Prior Publication Data
US 2011/0207939 A1 Aug. 25, 2011

Related U.S. Application Data

(63) Continuation of application No. 11/597,335, filed as application No. PCT/US2005/019394 on Jun. 2, 2005, now abandoned.

(60) Provisional application No. 60/576,382, filed on Jun. 2, 2004.

(51) Int. Cl.
*A61K 31/69* (2006.01)
*C07F 5/02* (2006.01)

(52) U.S. Cl. ............... 514/64; 564/8; 564/305

(58) Field of Classification Search .............. 564/8, 305; 548/304.4, 310.7; 514/64
See application file for complete search history.

(56) References Cited

U.S. PATENT DOCUMENTS

| | | | |
|---|---|---|---|
| 6,867,200 B1 | 3/2005 | Allen et al. | |
| 7,479,502 B2 | 1/2009 | Kolesnikov et al. | |
| 2003/0114457 A1 | 6/2003 | Hu et al. | |
| 2005/0176797 A1 | 8/2005 | Hu et al. | |
| 2005/0203094 A1 | 9/2005 | Kolesnikov et al. | |
| 2006/0205942 A1 | 9/2006 | Kolesnikov et al. | |
| 2008/0275250 A1 | 11/2008 | Dickman | |
| 2009/0054432 A1 | 2/2009 | Kolesnikov et al. | |
| 2010/0298396 A1 | 11/2010 | Loury et al. | |
| 2011/0269806 A1 | 11/2011 | Kolesnikov et al. | |

FOREIGN PATENT DOCUMENTS

| | | |
|---|---|---|
| WO | WO-00-35886 A2 | 6/2000 |
| WO | WO-00-35886 A3 | 6/2000 |
| WO | WO-02-14274 A1 | 2/2002 |
| WO | WO-02-14307 A1 | 2/2002 |
| WO | WO-03-006011 A1 | 1/2003 |
| WO | WO-03-006670 A2 | 1/2003 |
| WO | WO-03-006670 A3 | 1/2003 |
| WO | WO-03-068756 A1 | 8/2003 |
| WO | WO-2004-050637 A2 | 6/2004 |
| WO | WO-2004-050637 A3 | 6/2004 |
| WO | WO-2004-062661 A1 | 7/2004 |
| WO | WO-2005-118554 A2 | 12/2005 |
| WO | WO-2005-118554 A3 | 12/2005 |
| WO | WO-2005-121102 A2 | 12/2005 |
| WO | WO-2005-121102 A3 | 12/2005 |
| WO | WO-2009-052323 A2 | 4/2009 |
| WO | WO-2009-052323 A3 | 4/2009 |

OTHER PUBLICATIONS

Kolesnikov et al (2004): STN International HCAPLUS database, Columbus (OH), accession No. 2004: 610079.*
Katz, B.A. et al., "A novel serine protease inhibition motif involving a multi-centered short hydrogen bonding network at the active site," J. Mol. Biol. 307(5):1451-1486 (2001).
Katz, B.A. et al., "Engineering inhibitors highly selective for the S1 sites of Ser190 trypsin-like serine protease drug targets," Chem. Biol. 8(11):1107-1121 (2001).
Kolesnikov et al. STN International HCAPLUS databased, 2004, Accession No. 2004:493686, Columbus, Ohio.
Sendzik, M. et al., "Environmentally friendly and efficient: iron-mediated reduction of 3-methyl-5-aryl-1,2,4-oxadiazoles to benzamidines," Tetrahedron Lett. 44(48):8697-8700 (2003).
Verner, E. et al., "Development of serine protease inhibitors displaying a multicentered shor (<2.3.ANG.) hydrogen bond binding mode: Inhibitors of urokinase-type plasminogen activator and factor Xa," J. Med. Chem. 44:2753-2771 (2001).
Young et al., "Optimization of a screening lead for factor VIIa/TF," Bioorg. Med. Chem. Ltrs. 11(17):2253-2256 (2001).
PCT/US2005/019394 IPRP dated Dec. 4, 2006.
PCT/US2005/019394 International Search Report dated Jan. 16, 2006.
Cancer, http://www.hlm.nih.gove/medlineplus/cancer.html, 2009, [retrieved from the Internet on Mar. 17, 2009].
Golub et al. "Molecular Classification of Cancer: Class Discovery and Class Prediction by Gene Expression Monitoring." *Science*, 1999, 286:521-537.
Lala et al. "Role of Nitric Oxide in Tumor Progression: Lessons from Experimental Tumors." *Cancer Metastasis Reviews*, 1998, 17(1):91-106.
Sausville et al. "Contributions of Human Tumor Xenografts to Anticancer Drug Development." *Cancer Res*, 2006, 66(7):3351-3354.
PCT/US03/39635 Search Report dated Sep. 2, 2004. PCT/US08/80221 Search Report and Written Opinion dated Jul. 29, 2009.
PCT/US08/80221 IPRP dated Apr. 20, 2010.
EP08839610.6 Search Report dated Mar. 7, 2011.

* cited by examiner

*Primary Examiner* — Golam M M Shameem
(74) *Attorney, Agent, or Firm* — Wilson, Sonsini, Goodrich & Rosati

(57) ABSTRACT

The present invention relates to novel inhibitors of Factors VIIa, IXa, Xa, XIa, in particular Factor VIIa, pharmaceutical compositions comprising these inhibitors, and methods for using these inhibitors for treating or preventing thromboembolic disorders, cancer or rheumatoid arthritis. Processes for preparing these inhibitors are also disclosed.

3 Claims, No Drawings

FACTOR VIIA INHIBITOR

RELATED APPLICATIONS

This application is continuation of U.S. patent application Ser. No. 11/597,335 filed Jul. 14, 2008, now abandoned which is a 371 national phase application of PCT/US2005/019394 filed Jun. 2, 2005, which claims benefit of U.S. Patent Application No. 60/576,382, filed Jun. 2, 2004 all of which are herein incorporation by reference in their entirety.

BACKGROUND OF THE INVENTION

1. Field of Invention

The present invention relates to novel inhibitors of Factor VIIa, pharmaceutical compositions comprising these inhibitors, and methods for using these inhibitors for treating or preventing disorders mediated by Factor VIIa. Processes for preparing these inhibitors are also disclosed.

2. State of the Art

Thrombosis results from a complex sequence of biochemical events, known as the coagulation cascade. A triggering event in coagulation is the binding of the serine protease Factor VIIa (FVIIa), found in the circulation, to tissue factor (TF), a receptor, which is found on the surface of blood vessels after damage or inflammation. Once bound to TF, Factor VIIa catalyzes the formation of the serine protease Factor Xa, which subsequently forms the final protease in the cascade, thrombin.

The clinical manifestations of thrombosis range from acute myocardial infarction (AMI or heart attack) and unstable angina (UA), which occur in the key blood vessels of the heart (coronary vasculature) to deep vein thrombosis (DVT), which is the formation of blood clots in lower extremities and which often follows orthopedic surgery on the hip and knee, as well as general abdominal surgery and paralysis. Formation of DVT is a risk factor for the development of pulmonary embolism (PE) in which part of a blood clot formed in the lower extremities breaks off and travels to the lung where it blocks the flow of blood. The unpredictable development of PE often leads to a fatal outcome. Thrombosis can also be generalized systemically, with microclot formation occurring throughout the vascular system. This condition, known as disseminated intravascular coagulation (DIC), can be a consequence of certain viral diseases such as Ebola, certain cancers, sepsis, and rheumatoid arthritis. Severe DIC can lead to a dramatic reduction in the coagulation factors due to the excessive activation of the clotting response that may result in multiple organ failure, hemorrhage, and death.

The formation or embolization of blood clots in the blood vessels of the brain is the key event resulting in ischemic stroke. Triggering factors that lead to stroke are atrial fibrillation or abnormal rhythm of the atria of the heart and atherosclerosis followed by thrombosis in the main artery leading from the heart to the brain (carotid artery). Over 600,000 individuals suffer strokes each year in the U.S. Two-thirds of these stroke victims suffer some disability, and one-third suffer permanent and severe disability. Accordingly, there is a need for antithrombotic agents for the treatment of a variety of thrombotic conditions. The present invention fulfills this and related needs.

SUMMARY OF THE INVENTION

In one aspect this invention is directed to a compound of Formula I:

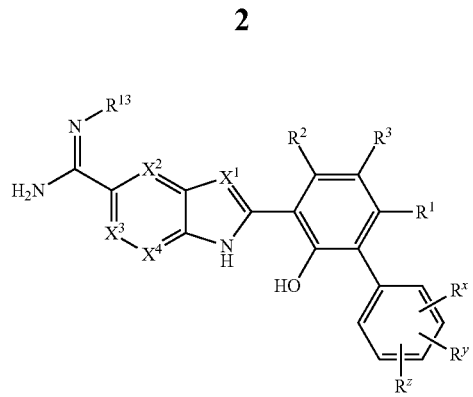

wherein:

$X^1$, $X^2$, $X^3$, and $X^4$ are independently —N— or —CR$^4$— wherein R$^4$ is hydrogen, alkyl, or halo with the proviso that not more than three of $X^1$, $X^2$, $X^3$ and $X^4$ are —N—;

R$^1$ is hydrogen, alkyl, halo, carboxy or aminocarbonyl;

R$^2$ is hydrogen, alkyl, or halo;

R$^3$ is dicarboxyalkylaminocarbonylalkyl or dicarboxyalkylaminocarbonylcycloalkyl;

R$^x$ is hydrogen, alkyl, alkylthio, halo, hydroxy, hydroxyalkyl, alkoxy, aminosulfonyl, alkylaminosulfonyl, dialkylaminosulfonyl, or nitro;

R$^y$ is hydrogen, alkyl, or halo;

R$^z$ is hydrogen, alkyl, haloalkyl, cycloalkyl, alkylthio, halo, hydroxy, hydroxyalkyl, nitro, cyano, alkoxy, alkoxyalkyl, alkoxyalkyloxy, hydroxyalkyloxy, aminoalkyloxy, carboxyalkyloxy, aminocarbonylalkyloxy, haloalkoxy, carboxy, carboxyalkyl, alkoxycarbonyl, alkoxycarbonylalkyl, cyanoalkyl, alkylsulfonyl, alkylsulfonylalkyl, arylsulfonyl, heteroarylsulfonyl, carbamimidoyl, hydroxy-carbamimidoyl, alkoxycarbamimidoyl, alkylsulfonylamino, alkylsulfonylaminoalkyl, alkoxysulfonylamino, alkoxysulfonylaminoalkyl, heterocycloalkylalkylaminocarbonyl, hydroxyalkoxyalkylaminocarbonyl, heterocycloalkylcarbonyl, heterocycloalkylcarbonyl-alkyl, heterocycloalkyl, heterocycloalkylalkyl, oxoheterocycloalkyl, oxoheterocycloalkyl-alkyl, heteroaryl, heteroaralkyl, ureido, alkylureido, dialkylureido, ureidoalkyl, alkylureidoalkyl, dialkylureidoalkyl, thioureido, thioureidoalkyl, —COR$^{12}$ (where R$^{12}$ is alkyl, haloalkyl, hydroxyalkyl, alkoxyalkyl, or aminoalkyl), -(alkylene)-COR$^{12}$ (where R$^{12}$ is alkyl, haloalkyl, hydroxyalkyl, alkoxyalkyl, or aminoalkyl), —CONR$^{14}$R$^{15}$ (where R$^{14}$ is hydrogen or alkyl and R$^{15}$ is hydrogen, alkyl, hydroxyalkyl, alkoxyalkyl, aryl, aralkyl, heteroaryl, or heteroaralkyl), -(alkylene)-CONR$^{16}$R$^{17}$ (where R$^{t6}$ is hydrogen, alkyl or hydroxyalkyl and R$^{17}$ is hydrogen, alkyl, hydroxyalkyl, alkoxyalkyl, aryl, aralkyl, heteroaryl, or heteroaralkyl), —NR$^{18}$R$^{19}$ (where R$^{18}$ is hydrogen or alkyl and R$^{19}$ is hydrogen, alkyl, acyl, aryl, aralkyl, heteroaryl, or heteroaralkyl), -(alkylene)-NR$^{20}$R$^{21}$ (where R$^{20}$ is hydrogen, alkyl, or hydroxyalkyl and R$^{21}$ is hydrogen, alkyl, acyl, alkoxycarbonyl, hydroxyalkyl, alkoxyalkyl, aryl, aralkyl, heteroaryl, or heteroaralkyl), —SO$_2$NR$^{22}$R$^{23}$ (where R$^{22}$ is hydrogen or alkyl and R$^{23}$ is hydrogen, alkyl, aryl, aralkyl, heteroaryl, or heteroaralkyl, or R$^{22}$ and R$^{23}$ together with the nitrogen atom to which they are attached form heterocycloamino), -(alkylene)-SO$_2$NR$^{24}$R$^{25}$ (where R$^{24}$ is hydrogen or alkyl and R$^{25}$ is hydrogen, alkyl, aryl, aralkyl, heteroaryl, or heteroaralkyl or R$^{24}$ and R$^{25}$ together with the nitrogen atom to which they are attached form heterocycloamino), —NR$^{26}$SO$_2$NR$^{27}$R$^{28}$ (where R$^{26}$ and R$^{27}$ are independently hydrogen or alkyl, and R$^{28}$ is hydrogen, alkyl, aryl, aralkyl, heteroaryl, or heteroaralkyl or R$^{27}$ and R$^{28}$ together with the nitrogen atom to which they are attached form heterocycloamino), -(alkylene)-$NR^{29}SO_2NR^{30}R^{31}$ (where $R^{29}$ and $R^{30}$ are independently hydrogen or alkyl, and $R^{31}$ is hydrogen, alkyl, aryl, aralkyl, heteroaryl, or heteroaralkyl or $R^{30}$ and $R^{31}$ together with the nitrogen atom to which they are attached form heterocycloamino), —CONH-(alkylene)-$NR^{32}R^{33}$ where $R^{32}$ is hydrogen or alkyl and $R^{33}$ is alkyl), or aralkyl; and $R^{13}$ is hydrogen, hydroxy, $(C_{1-10})$alkoxy, —$C(O)R^{35}$ where $R^{35}$ is alkyl, aryl, haloalkyl, or cyanoalkyl, or —$C(O)OR^{36}$ where $R^{36}$ is alkyl, hydroxyalkyl, alkoxyalkyl, alkoxycarbonylalkyl, acyl, aryl, or haloalkyl; or a zwitterions thereof; or a pharmaceutically acceptable salt thereof provided that the compound of Formula I is not (RS)-2-{2-[5-(5-carbamimidoyl-1H-benzimidazol-2-yl)-6,2'-dihydroxy-5'-sulfamoylbiphenyl-3-yl]acetylamino}succinic acid; (RS)-2-{2-[5-(5-carbamimidoyl-1H-benzimidazol-2-yl)-6,2'-dihydroxy-5'-sulfamoylbiphenyl-3-yl]-2-methylpropionylamino}succinic acid; and (RS)-2-{2-[5-(5-carbamimidoyl-1H-benzimidazol-2-yl)-6,2'-dihydroxy-5'-ureidomethyl]biphenyl-3-yl]-2-methylpropionylamino}succinic acid or a pharmaceutically acceptable salt thereof. The names of the compounds were generated using AutoNom version 2.2.

In a second aspect, this invention is directed to a pharmaceutical composition comprising a pharmaceutically acceptable carrier and a therapeutically effective amount of a compound of Formula I, or a zwitterion thereof, or a pharmaceutically acceptable salt thereof.

In a third aspect, this invention is directed to a method of treating a disease in an animal that is mediated by Factors VIIa, IXa, Xa and/or XIa, preferably VIIa, which method comprises administering to said animal a therapeutically effective amount of a compound of Formula I, or a zwitterions thereof, or a pharmaceutically acceptable salt thereof. Preferably, the disorder is a thromboembolic disorder or cancer or rheumatoid arthritis, more preferably a thromboembolic disorder, even more preferably the disorder is deep vein thrombosis. Preferably, the compound of the invention is administered prophylactically.

In a fourth aspect, this invention is directed to a method of treating a thromboembolic disorder in an animal which method comprises administering to said animal a therapeutically effective amount of a compound of Formula I, or a zwitterion thereof, or a pharmaceutically acceptable salt thereof in combination with another anticoagulant agent(s) independently selected from a group consisting of a thrombin inhibitor, factor IXa inhibitor, factor Xa inhibitor, Aspirin®, and Plavix®.

In a fifth aspect, this invention is directed to a method for inhibiting the coagulation of a biological sample (e.g., stored blood products and samples) comprising the administration of a compound of Formula I, or a zwitterion thereof, or a pharmaceutically acceptable salt thereof.

In a sixth aspect, this invention directed to the use of a compound of Formula I, or a zwitterion thereof, or a pharmaceutically acceptable salt thereof in the preparation of a medicament. The medicament is useful in the treatment of a thromboembolic disorder or cancer or rheumatoid arthritis in an animal. Preferably, the disorder is a thromboembolic disorder such as deep vein thrombosis.

In a seventh aspect, this invention is directed to an intermediate of formula (II):

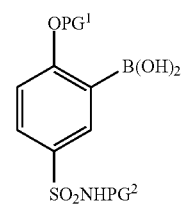

(II)

where $PG^1$ is a suitable oxygen-protecting group and $PG^2$ is a suitable amino-protecting group. Preferably, $PG^1$ is alkyl or aralkyl, more preferably benzyl. Preferably, $PG^2$ is alkyl, more preferably tert-butyl.

In an eighth aspect, this invention is directed to a process of preparing a compound of Formula I where $R^3$ is dicarboxyalkylaminocarbonylalkyl comprising:

(i) reacting a compound of formula:

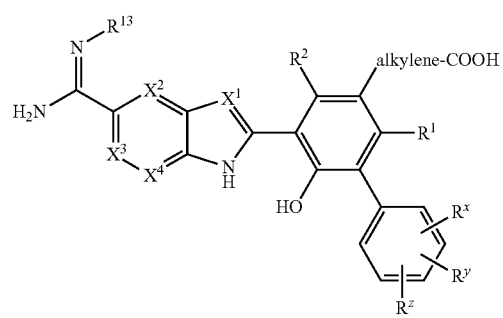

where $R^1$, $R^2$, $R^{13}$, $R^x$, $R^y$, $R^z$, $X^1$-$X^4$ are as defined in the Summary of the Invention or a suitably protected derivative thereof; with dicarboxyalkylamino where the carboxy groups are optionally protected;

(ii) optionally removing the any protecting groups;

(iii) optionally modifying any of the $R^1$, $R^2$, $R^{13}$, $R^x$, $R^y$, and $R^z$ groups;

(iii) optionally converting the product from step (ii) or (iii) above, to an acid addition salt;

(iv) optionally converting the product from step (ii) or (iii) above, to a free base;

(v) optionally converting the product from step (ii) or (iii) above, to a zwitterions.

In a ninth aspect, this invention is directed to a process of preparing a compound of Formula Ib or Ic:

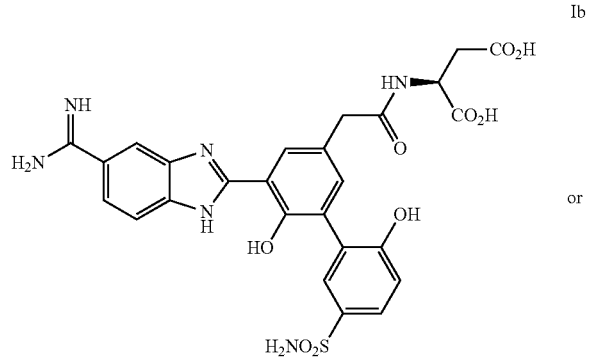

Ib or

-continued

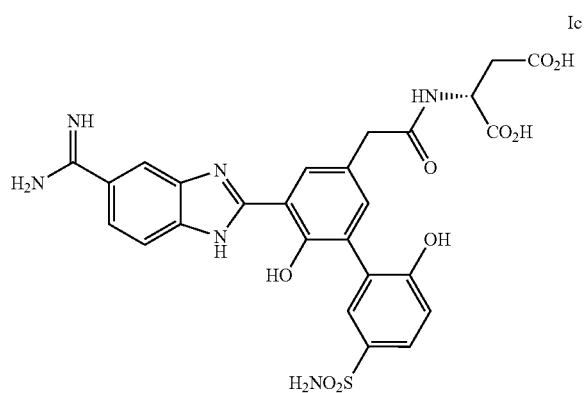

comprising:

reacting a compound of formula:

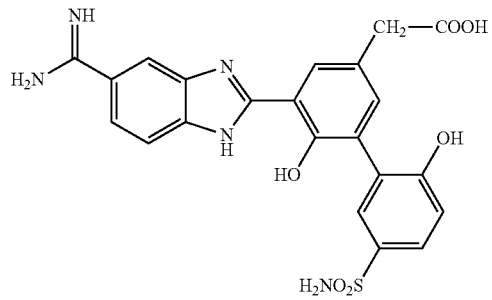 [SMILES: N=C(N)c1ccc2[nH]c(-c3cc(CC(=O)O)cc(-c4cc(S(N)(=O)=O)ccc4O)c3O)nc2c1]

with (R) or (S) aspartic acid respectively, where the carboxy groups are optionally protected;

(ii) optionally deprotecting any protected carboxy group(s);

(ii) optionally converting the product from step (i) or (ii) above, to an acid addition salt;

(iii) optionally converting the product from step (i) or (ii) above, to a free base;

(iv) optionally converting the product from step (i) or (ii) above, to a zwitterion; optionally deprotecting any protected carboxy group(s).

Preferably, the carboxy groups are protected with benzyl groups and the compound being prepared is Ib.

In a tenth aspect, this invention is directed to a method of preparing an intermediate of formula (II):

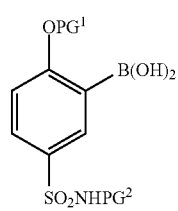

(II)

where $PG^1$ is a suitable oxygen-protecting group and $PG^2$ is a suitable amino-protecting group comprising:

(i) reacting a compound of formula (III):

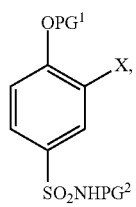

where $PG^1$ and $PG^2$ is are as defined above and X is halo; with one equivalent of an organometallic agent of formula RLi or $RMgX^1$ where R is alkyl or aryl and $X^1$ is halo to deprotonate the —$SO_2NHPG^2$ group;

(ii) transmetallating the compound generated in Step (i) above with one equivalent of an organometallic agent of formula RLi or $RMgX^1$ where R is alkyl or aryl;

(iii) treating the compound generated in Step (ii) above with trialkylborate to generate a compound of formula (II).

Preferably, methylmagnesium bromide is used in Step (i) above; i-propylmagnesium bromide is used in Step (ii) above and the trialkylborate is trimethylborate. Preferably, in compound (III) above, $PG^1$ is benzyl, $PG^2$ is tert-butyl and X is iodo.

DETAILED DESCRIPTION OF THE INVENTION

Definitions

The following terms, as used in the present specification and claims, are intended to have the meanings as defined below, unless indicated otherwise or used in naming a compound.

"Alkyl" means a linear saturated monovalent hydrocarbon radical of one to six carbon atoms or a branched saturated monovalent hydrocarbon radical of three to six carbon atoms, e.g., methyl, ethyl, propyl, 2-propyl, butyl (including all isomeric forms), pentyl (including all isomeric forms), and the like.

"Alkylene" means a linear saturated divalent hydrocarbon radical of one to six carbon atoms or a branched saturated divalent hydrocarbon radical of three to six carbon atoms e.g., methylene, ethylene, propylene, 1-methylpropylene, 2-methylpropylene, butylene, pentylene, and the like.

"Alkylthio" means a radical —SR where R is alkyl as defined above, e.g., methylthio, ethylthio, propylthio (including all isomeric forms), butylthio (including all isomeric forms), and the like.

"Amino" means the radical —NRR' where R and R' are independently hydrogen, alkyl, or —$COR^a$ where $R^a$ is alkyl, e.g., —$NH_2$, methylaminoethyl, 1,3-diaminopropyl, acetylaminopropyl, and the like.

"Alkylamino" means a radical —NHR where R is alkyl as defined above, e.g., methylamino, ethylamino, propylamino (including all isomeric forms), and the like.

"Acyl" means a radical —COR' where R' is alkyl, alkoxy, haloalkyl, aminoalkyl, hydroxyalkyl, or alkoxyalkyl as defined herein, e.g., acetyl, trifluoroacetyl, hydroxymethylcarbonyl, and the like.

"Aminosulfonyl" or "sulfamoyl" means a radical —$SO_2NH_2$.

"Alkylaminosulfonyl" means a radical —$SO_2NHR$ where R is alkyl as defined above, e.g., methylaminosulfonyl, ethylamino-sulfonyl, and the like.

"Alkylsulfonyl" means a radical —$SO_2R$ where R is alkyl as defined above, e.g., methylsulfonyl, ethylsulfonyl, n- or iso-propylsulfonyl, and the like.

"Alkylsulfonylalkyl" means a radical -(alkylene)-SO$_2$R where R is alkyl as defined above, e.g., methylsulfonylmethyl, ethylsulfonylmethyl, n- or iso-propylsulfonylethyl, and the like.

"Alkylsulfonylamino" means a radical —NHSO$_2$R where R is alkyl as defined above, e.g., methylsulfonylamino, ethylsulfonylamino, n- or iso-propylsulfonylamino, and the like.

"Alkylsulfonylaminoalkyl" means a radical -(alkylene)-NHSO$_2$R where R is alkyl as defined above, e.g., methylsulfonylaminomethyl, ethylsulfonylaminomethyl, n- or iso-propylsulfonylaminoethyl, and the like.

"Alkoxysulfonylamino" means a radical —NHSO$_2$R where R is alkoxy as defined herein, e.g., methoxysulfonylamino, ethoxysulfonylamino, and the like.

"Alkoxysulfonylaminoalkyl" means a radical -(alkylene)-NHSO$_2$R where R is alkoxy as defined herein, e.g., methoxysulfonylaminomethyl, ethoxysulfonylaminomethyl, and the like.

"Alkoxy" means a radical —OR where R is alkyl as defined above, e.g., methoxy, ethoxy, propoxy, or 2-propoxy, n-, iso-, or tert-butoxy, and the like.

"Alkoxycarbonyl" means a radical —COOR where R is alkyl as defined above, e.g., methoxycarbonyl, ethoxycarbonyl, and the like.

"Alkoxycarbonylalkyl" means a radical -(alkylene)-COOR where R is alkyl as defined above, e.g., methoxycarbonylmethyl, ethoxycarbonylmethyl, and the like.

"Alkoxyalkyl" means a linear monovalent hydrocarbon radical of one to six carbon atoms or a branched monovalent hydrocarbon radical of three to six carbons substituted with at least one alkoxy group, preferably one or two alkoxy groups, as defined above, e.g., 2-methoxyethyl, 1-, 2-, or 3-methoxypropyl, 2-ethoxyethyl, and the like.

"Aminoalkyl" means a linear monovalent hydrocarbon radical of one to six carbon atoms or a branched monovalent hydrocarbon radical of three to six carbons substituted with at least one, preferably one or two, —NRR' where R and R' are independently hydrogen, alkyl, or —COR$^a$ where R$^a$ is alkyl, e.g., aminomethyl, methylaminoethyl, 1,3-diaminopropyl, acetylaminopropyl, and the like.

"Aminocarbonylalkyl" means a linear monovalent hydrocarbon radical of one to six carbon atoms or a branched monovalent hydrocarbon radical of three to six carbons substituted with one or two —CONRR' where R and R' are independently hydrogen, alkyl, or —COR$^a$ where R$^a$ is alkyl, e.g., aminocarbonylmethyl, methylaminocarbonylmethyl, acetylaminocarbonylpropyl, and the like.

"Alkoxyalkyloxy" means a radical —OR where R is alkoxyalkyl, as defined above, e.g., 2-methoxyethyloxy, 1-, 2-, or 3-methoxypropyloxy, 2-ethoxyethyloxy, and the like.

"Aminoalkyloxy" means a radical —OR where R is aminoalkyl, as defined above, e.g., 2-aminoethyloxy, 1-, 2-, or 3-methylaminopropyloxy, and the like.

"Aminocarbonyl" or "carbamoyl" means a radical —CONH$_2$.

"Aminocarbonylalkyloxy" means a radical —O-(alkylene)-CONRR" where R and R' are independently hydrogen or alkyl, as defined above, e.g., 2-aminocarbonylethyloxy, aminocarbonylmethyloxy, and the like.

"Alkylureido" means a radical —NRCONHR' where R is hydrogen or alkyl and R' is alkyl, e.g., methylureidomethyl, and the like.

"Alkylureidoalkyl" means a radical -(alkylene)-NRCONHR' where R is hydrogen or alkyl and R' is alkyl, e.g., methylureidomethyl, and the like.

"Aryl" means a monovalent monocyclic or bicyclic aromatic hydrocarbon radical of 6 to 12 ring atoms, and optionally substituted independently with one or more substituents, preferably one, two, or three substituents, selected from alkyl, haloalkyl, alkoxy, alkylthio, halo, nitro, —COR (where R is alkyl), cyano, amino, alkylamino, dialkylamino, hydroxy, carboxy, or —COOR where R is alkyl. Representative examples include, but are not limited to, phenyl, biphenyl, 1-naphthyl, and 2-naphthyl and the derivatives thereof.

"Arylsulfonyl" means a radical —SO$_2$R where R is aryl as defined above, e.g., phenylsulfonyl, and the like.

"Aralkyl" means a radical -(alkylene)-R where R is an aryl group as defined above e.g., benzyl, phenylethyl, 3-(3-chlorophenyl)-2-methylpentyl, and the like.

"Alkoxycarbamimidoyl" means a radical —C(=NH)NHOR or —C(=NOR)NH$_2$ where R is alkyl as defined above, e.g., methoxycarbamimidoyl.

"Cycloalkyl" means a cyclic saturated monovalent hydrocarbon radical of three to six carbon atoms, e.g., cyclopropyl, cyclobutyl, and the like, preferably cyclopropyl.

"Carboxyalkyl" means a radical -(alkylene)-COOH, e.g., carboxymethyl, carboxyethyl, 1-, 2-, or 3-carboxypropyl, and the like.

"Carboxyalkyloxy" means a radical —O-(alkylene)-COOH, e.g., carboxymethyloxy, carboxyethyloxy, and the like.

"Carbamimidoyl" means a radical —C(=NH)NH$_2$, or a protected derivative thereof.

"Cyanoalkyl" means a radical -(alkylene)-CN, e.g., cyanomethyl, cyanoethyl, cyanopropyl, and the like.

"Dicarboxyalkylaminocarbonylalkyl" means a radical -(alkylene)-CONHR where R is alkyl, as defined herein, substituted with two carboxy groups, e.g., —CH$_2$CONHCH(COOH)(CH$_2$COOH), —CH$_2$CONHCH(CH$_2$COOH)$_2$, —C(CH$_3$)$_2$—CONHCH(COOH)(CH$_2$COOH), —C(CH$_3$)$_2$—CONHCH(CH$_2$COOH)$_2$, and the like.

"Dicarboxyalkylamino" means a radical —NHR where R is alkyl, as defined herein, substituted with two carboxy groups "Dicarboxyalkyaminocarbonylcycloalkyl" means radical of the formula:

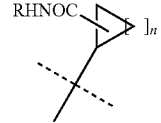

where n is 1 to 4 and R is alkyl, as defined herein, substituted with two carboxy groups.

"Dialkylamino" means a radical —NRR' where R and R' are independently alkyl as defined above, e.g., dimethylamino, methylethylamino, methylopropylamino (including all isomeric forms), and the like.

"Dialkylaminosulfonyl" means a radical —SO$_2$NRR' where R and R' are independently alkyl as defined above, e.g., dimethylaminosulfonyl, methylethylamino-sulfonyl, and the like.

"Dialkylureido" means a radical —NRCONR'R" where R is hydrogen or alkyl and R' and R" are independently alkyl, e.g., dimethylureido, and the like.

"Dialkylureidoalkyl" means a radical -(alkylene)-NRCONR'R" where R is hydrogen or alkyl and R' and R" are independently alkyl, e.g., dimethylureidomethyl, and the like.

"Guanidinoalkyl" means a linear monovalent hydrocarbon radical of one to six carbon atoms or a branched monovalent hydrocarbon radical of three to six carbons substituted with at least one, preferably one or two, —NRC(NRR')NRR' where R and R' are independently hydrogen, alkyl, or —COR$^a$ where R$^a$ is alkyl, e.g., guanidinomethyl, N'-methylaminoethyl, 2-(N',N',N'',N''-tetramethyl-guanidino)-ethyl, and the like.

"Halo" means fluoro, chloro, bromo, and iodo, preferably fluoro or chloro.

"Haloalkyl" means alkyl substituted with one or more halogen atoms, preferably one to three halogen atoms, preferably fluorine or chlorine, including those substituted with different halogens, e.g., —CH$_2$Cl, —CF$_3$, —CHF$_2$, and the like.

"Haloalkoxy" means a radical —OR where R is haloalkyl as defined above, e.g., —OCH$_2$Cl, —OCF$_3$, —OCHF$_2$, and the like.

"Hydroxyalkyl" means a linear monovalent hydrocarbon radical of one to six carbon atoms or a branched monovalent hydrocarbon radical of three to six carbons substituted with one to five hydroxy groups, provided that if two hydroxy groups are present they are not both on the same carbon atom. Representative examples include, but are not limited to, hydroxymethyl, 2-hydroxyethyl, 2-hydroxypropyl, 3-hydroxypropyl, 1-(hydroxymethyl)-2-methylpropyl, 2-hydroxybutyl, 3-hydroxybutyl, 4-hydroxybutyl, 2,3-dihydroxypropyl, 1-(hydroxymethyl)-2-hydroxyethyl, 2,3-dihydroxybutyl, 3,4-dihydroxybutyl and 2-(hydroxymethyl)-3-hydroxypropyl, preferably 2-hydroxyethyl, 2,3-dihydroxypropyl, and 1-(hydroxymethyl)-2-hydroxyethyl.

"Hydroxyalkyloxy" means a radical —OR where R is hydroxyalkyl as defined above, e.g., 2-hydroxyethyloxy, 3-hydroxypropyloxy, and the like.

"Hydroxyalkoxyalkylaminocarbonyl" means a radical —CONH-(alkylene)-O-(alkylene)OH where alkylene is as defined above, e.g., —CONH—(CH$_2$)$_2$—O—(CH$_2$)$_2$OH and the like.

"Heterocycloalkyl" means a saturated or unsaturated monovalent cyclic group of 3 to 8 ring atoms in which one or two ring atoms are heteroatoms selected from N, O, or S(O)n, where n is an integer from 0 to 2, the remaining ring atoms being C. The heterocycloalkyl ring may be optionally substituted with one or more substituents, preferably one or two substituents, independently selected from alkyl, aryl, heteroaryl, aralkyl, 3,5,6-trihydroxy-2-hydroxymethyl-tetrahydropyran-3-yl, 4,5-dihydroxy-2-hydroxymthyl-6-(4,5,6-trihydroxy-2-hydroxymthyl-tetrahydro-pyran-3-yloxy)-tetrahydro-pyran-3-yl, heteroaralkyl, halo, haloalkyl, hydroxy, hydroxyalkyl, alkoxy, alkoxyalkyl, aminoalkyl, guanidinoalkyl, halo, cyano, carboxy, —COOR (where R is alkyl as define above), or —CONR$^a$R$^b$ (where R$^a$ and R$^b$ are independently hydrogen or alkyl), or a protected derivative thereof. More specifically the term heterocycloalkyl includes, but is not limited to, pyrrolidino, piperidino, morpholino, piperazino, tetrahydropyranyl, and thiomorpholino.

"Heterocycloalkylcarbonyl" means a radical —COR where R is heterocycloalkyl as defined above. More specifically the term heterocycloalkylcarbonyl includes, but is not limited to, 1-pyrrolidinocarbonyl, 1-piperidinocarbonyl, 4-morpholinocarbonyl, 1-piperazinocarbonyl, 2-tetrahydropyranylcarbonyl, and 4-thiomorpholinocarbonyl, and the derivatives thereof.

"Heterocycloalkylcarbonylalkyl" means a radical -(alkylene)-COR where R is heterocycloalkyl as defined above. More specifically the term heterocycloalkylcarbonyl includes, but is not limited to, 1-pyrrolidinocarbonylmethyl, 1-piperidinocarbonylmethyl, 4-morpholinocarbonylethyl, 1-piperazinocarbonylmethyl, and the derivatives thereof.

"Heterocycloalkylalkyl" means a radical -(alkylene)-R where R is heterocycloalkyl as defined above. More specifically the term heterocycloalkylalkyl includes, but is not limited to, pyrrolidin-1-ylmethyl, piperidin-1-ylmethyl, 2-morpholin-1-ylethyl, piperazin-1-ylethyl, and the derivatives thereof.

"Heterocycloalkylalkylaminocarbonyl" means a radical —CONH-(alkylene)-R where R is heterocycloalkyl as defined above. More specifically the term heterocycloalkylalkylamino-carbonyl includes, but is not limited to, 1-pyrrolidinoethyl-aminocarbonyl, 1-piperidinoethyl-aminocarbonyl, 4-morpholinoethylcarbonyl, 1-piperazinoethylaminocarbonyl, and 4-thiomorpholinopropylaminocarbonyl, and the derivatives thereof.

"Heteroaryl" means a monovalent monocyclic or bicyclic aromatic radical of 5 to 10 ring atoms containing one or more, preferably one or two ring heteroatoms selected from N, O, or S, the remaining ring atoms being carbon. The heteroaryl ring is optionally substituted with one or more substituents, preferably one or two substituents, independently selected from alkyl, haloalkyl, alkoxy, alkylthio, aminoalkyl, guanidinoalkyl, halo, nitro, cyano, amino, alkyl or dialkylamino, hydroxy, carboxy, or —COOR where R is alkyl as define above. More specifically the term heteroaryl includes, but is not limited to, pyridyl, pyrrolyl, imidazolyl, thienyl, furanyl, indolyl, quinolyl, pyrazine, pyrimidine, pyradizine, oxazole, isooxazolyl, benzoxazole, quinoline, isoquinoline, benzopyranyl, and thiazolyl.

"Heteroarylsulfonyl" means a radical —SO$_2$R where R is heteroaryl as defined above, e.g., pyridylsulfonyl, furanylsulfonyl, and the like.

"Heteroaralkyl" means a radical -(alkylene)-R where R is a heteroaryl group as defined above e.g., pyridylmethyl, furanylmethyl, indolylmethyl, pyrimidinylmethyl, and the like.

"Heterocycloamino" means a saturated or unsaturated monovalent cyclic group of 3 to 8 ring atoms in which one or two ring atoms are heteroatoms selected from N, O, or S(O)n, where n is an integer from 0 to 2, the remaining ring atoms being C provided that at least one of the heteroatom is nitrogen and wherein one or two carbon atoms are optionally replace by a carbonyl group. The heterocycloamino ring may be optionally substituted with one or more substituents, preferably one or two substituents, independently selected from alkyl, hydroxy, hydroxyalkyl, alkoxy, alkoxyalkyl, aminoalkyl, guanidinoalkyl, halo, haloalkyl, aryl, heteroaryl, aralkyl, heteroaralkyl, haloalkyl, halo, cyano, carboxy, —CONR$^a$R$^b$ (where R$^a$ and R$^b$ are independently hydrogen or alkyl), or —COOR where R is alkyl as define above. More specifically the term heterocycloamino includes, but is not limited to, pyrrolidino, piperidino, piperazino, and thiomorpholino, and the derivatives thereof.

"Hydroxycarbamimidoyl" means a radical —C(═NH)NHOH or —C(═NOH)NH$_2$.

The present invention also includes the prodrugs of compounds of Formula I. The term prodrug is intended to represent covalently bonded carriers, which are capable of releasing the active ingredient of Formula I, when the prodrug is administered to a mammalian subject. Release of the active ingredient occurs in vivo. Prodrugs can be prepared by techniques known to one skilled in the art. These techniques generally modify appropriate functional groups in a given compound. These modified functional groups however regenerate original functional groups by routine manipulation or in vivo. Prodrugs of compounds of Formula I include compounds wherein a hydroxy, carbamimidoyl, guanidino, amino, carboxylic, or a similar group is modified. Examples of prodrugs include, but are not limited to esters (e.g., acetate, formate, and benzoate derivatives), carbamates (e.g., N,N-dimethylaminocarbonyl) of hydroxy functional groups in compounds of Formula I and the like. Prodrugs of compounds of Formula I are also within the scope of this invention.

The present invention also includes (derivatives and protected derivatives of compounds of Formula I. For example, when compounds of Formula I contain an oxidizable nitrogen atom (e.g., when a compound of Formula I contains a pyridine, amino, alkylamino, piperidino, piperazino, morpholino, or dialkylamino group), the nitrogen atom can be converted to an N-oxide by methods well known in the art.

Also when compounds of Formula I contain groups such as hydroxy, carboxy, carbonyl, thiol or any group containing a nitrogen atom(s), these groups can be protected with a suitable protecting groups. A comprehensive list of suitable protective groups can be found in T. W. Greene, *Protective Groups in Organic Synthesis,* John Wiley & Sons, Inc. 1999, the disclosure of which is incorporated herein by reference in its entirety. The protected derivatives of compounds of Formula I can be prepared by methods well known in the art.

A "pharmaceutically acceptable salt" of a compound means a salt that is pharmaceutically acceptable and that possesses the desired pharmacological activity of the parent compound. Such salts include:

acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)-benzoic acid, cinnamic acid, mandelic acid, methanesulfonic acid, ethanesulfonic acid, 1,2-ethanedisulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, glucoheptonic acid, 4,4'-methylenebis-(3-hydroxy-2-ene-1-carboxylic acid), 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like. It is understood that the pharmaceutically acceptable salts are non-toxic. Additional information on suitable pharmaceutically acceptable salts can be found in *Remington's Pharmaceutical Sciences,* 17th ed., Mack Publishing Company, Easton, Pa., 1985, which is incorporated herein by reference.

The compounds of the present invention may have asymmetric centers. Compounds of the present invention containing an asymmetrically substituted atom may be isolated in optically active or racemic forms. It is well known in the art how to prepare optically active forms, such as by resolution of materials. Many geometric isomers of olefins, C=C double bonds, and the like can be present in the compounds described herein, and all such stable isomers are contemplated in the present invention. Cis and trans geometric isomers of the compounds of the present invention are described and may be isolated as a mixture of isomers or as separated isomeric forms. All chiral, enantiomeric, diastereomeric, racemic forms and all geometric isomeric forms of a structure (representing a compound of Formula I) are intended, unless the specific stereochemistry or isomeric form is specifically indicated.

Certain compounds of Formula I exist in tautomeric equilibrium. Compounds of Formula I, which exist as tautomers are named, illustrated or otherwise described in this application as one possible tautomer. However, it is to be understood that all possible tautomers are meant to be encompassed by such names, illustrations and descriptions and are within the scope of this invention. For example, in compound of Formula I, the group —C(=NR$^{13}$)NH$_2$ can tautomerize to —C(=NH)NHR$^{13}$ group. Additionally, as used herein the terms alkyl includes all the possible isomeric forms of said alkyl group albeit only a few examples are set forth. Furthermore, when the cyclic groups such as aryl, heteroaryl, heterocycloalkyl are substituted, they include all the positional isomers albeit only a few examples are set forth.

Certain compounds that contain a basic group such as an amine portion and an acid portion e.g., carboxylic acid portion, depending upon the pH of the solution, may exist as a free amine and a free carboxylic acid or as a zwitterion in which the amine is protonated to form an ammonium ion and the carboxylic acid is deprotonated to form a carboxylate ion. All such zwitterions are included in this invention.

"Oxoheterocycloalkyl" means a saturated or unsaturated (provided that it is not aromatic) monovalent cyclic group of 3 to 8 ring atoms in which one or two ring atoms are heteroatoms selected from N, O, or S(O)n, where n is an integer from 0 to 2, the remaining ring atoms being C wherein one or two of the carbon atoms is/are replaced with an oxo (C=O) group. The oxoheterocycloalkyl ring may be optionally substituted with one or more substituents, preferably one or two substituents, independently selected from alkyl, aryl, heteroaryl, aralkyl, heteroaralkyl, haloalkyl, halo, hydroxy, hydroxyalkyl, alkoxyalkyl, aminoalkyl, guanidinoalkyl, alkoxy, cyano, carboxy, or —COOR where R is alkyl as define above. More specifically the term heterocycloalkyl includes, but is not limited to, 2 or 3-oxopyrrolidin-1-yl, 2, 3, or 4-oxopiperidino, 3-oxomorpholino, 2-oxo-piperazino, 2-oxotetrahydropyranyl, 3-oxothiomorpholino, 2-imidazolidone, and the derivatives thereof.

"Oxoheterocycloalkylalkyl" means a radical -(alkylene)-R where R is a oxoheterocycloalkylalkyl group as defined above e.g., More specifically the term oxoheterocycloalkylalkyl; includes, but is not limited to, 2 or 3-oxopyrrolidin-1-yl-(methyl, ethyl, or propyl), 2, 3, or 4-oxopiperidin-1-yl-(methyl, ethyl, or propyl), 3-oxomorpholin4-yl-(methyl, ethyl, or propyl), 2-oxopiperazin-1-yl-(methyl, ethyl, or propyl), 2-oxotetrahydro-pyran-3-yl-(methyl, ethyl, or propyl), 3-oxothiomorpholin-4-yl-(methyl, ethyl, or propyl), 2-imidazolidon-1-yl-(methyl, ethyl, or propyl), and the derivatives thereof.

"Optional" or "optionally" means that the subsequently described event or circumstance may but need not occur, and that the description includes instances where the event or circumstance occurs and instances in which it does not. For example, "heterocycloalkyl group optionally mono- or di-substituted with an alkyl group" means that the alkyl may but need not be present, and the description includes situations where the heterocycloalkyl group is mono- or disubstituted with an alkyl group and situations where the heterocycloalkyl group is not substituted with the alkyl group.

A "pharmaceutically acceptable carrier or excipient" means a carrier or an excipient that is useful in preparing a pharmaceutical composition that is generally safe, non-toxic and neither biologically nor otherwise undesirable, and includes a carrier or an excipient that is acceptable for veterinary use as well as human pharmaceutical use. "A pharmaceutically acceptable carrier/excipient" as used in the specification and claims includes both one and more than one such excipient.

"Treating" or "treatment" of a disease includes:

(1) preventing the disease, i.e. causing the clinical symptoms of the disease not to develop in a mammal that may be exposed to or predisposed to the disease but does not yet experience or display symptoms of the disease;

(2) inhibiting the disease, i.e., arresting or reducing the development of the disease or its clinical symptoms; or (3) relieving the disease, i.e., causing regression of the disease or its clinical symptoms.

A "therapeutically effective amount" means the amount of a compound of Formula I that, when administered to a mammal for treating a disease, is sufficient to effect such treatment for the disease. The "therapeutically effective amount" will vary depending on the compound, the disease and its severity and the age, weight, etc., of the mammal to be treated.

"Thioureido" means a radical —NRC(S)NR'R" where R, R', and R" are independently hydrogen or alkyl.

"Thioureidoalkyl" means a radical -(alkylene)-NRC(S)NR'R" where alkylene is as defined above. Representative examples include but are not limited to thioureidomethyl, thioureidoethyl, and the like.

"Ureido" means a radical —NHCONH$_2$.

"Ureidoalkyl" means a radical -(alkylene)-NHCONH$_2$ where alkylene is as defined above. Representative examples include but are not limited to ureidomethyl, ureidoethyl, and the like.

Representative compounds of this invention where $R^1$, $R^2$ and $R^{3'}$ are hydrogen; $X^1$ is —N—, $X^2$, $X^3$, and $X^4$ are carbon are disclosed in Table I below.

TABLE I

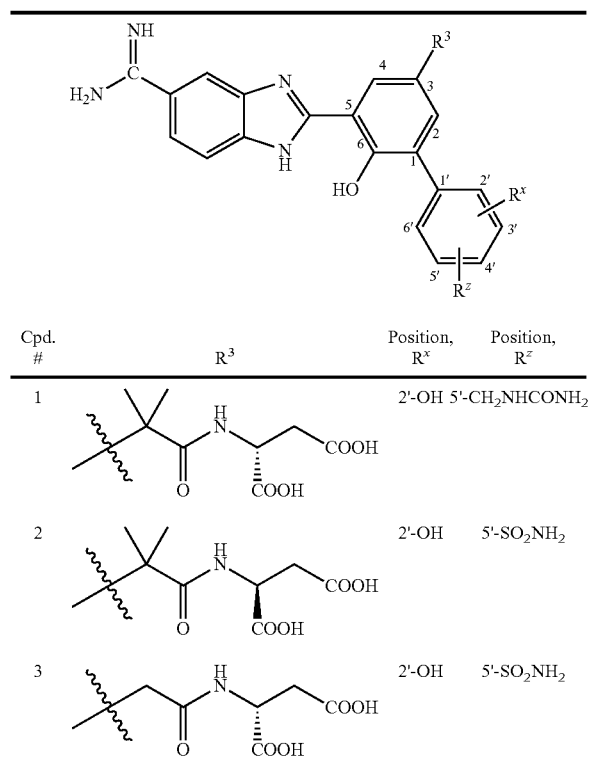

| Cpd. # | $R^3$ | Position, $R^x$ | Position, $R^z$ |
|---|---|---|---|
| 1 | | 2'-OH | 5'-CH$_2$NHCONH$_2$ |
| 2 | | 2'-OH | 5'-SO$_2$NH$_2$ |
| 3 | | 2'-OH | 5'-SO$_2$NH$_2$ |

TABLE I-continued

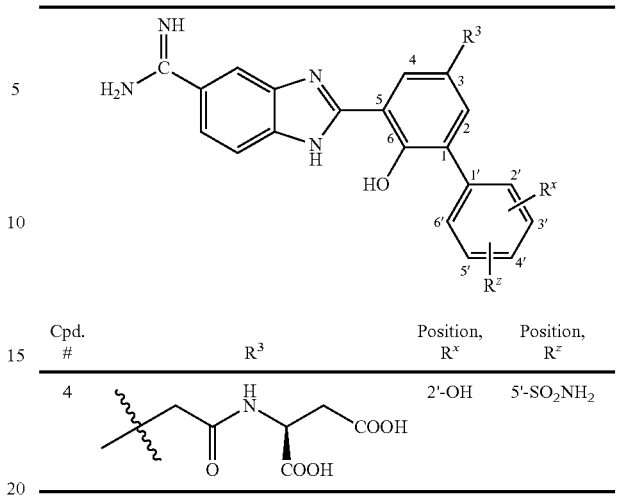

| Cpd. # | $R^3$ | Position, $R^x$ | Position, $R^z$ |
|---|---|---|---|
| 4 | | 2'-OH | 5'-SO$_2$NH$_2$ |

Preferred Embodiments

While the broadest definition of this invention is set forth in the Summary of the Invention, certain compounds of Formula I are preferred. For example:

(I) One preferred group of compounds is represented by the Formula Ia:

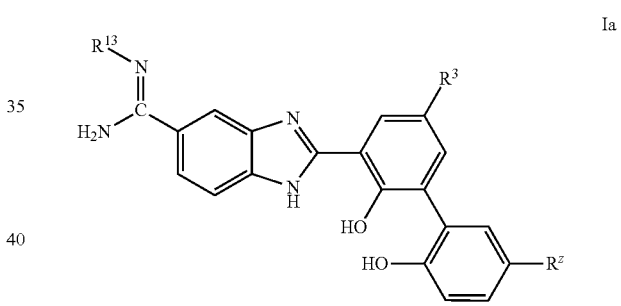

Ia wherein $R^3$, $R^{13}$ and $R^z$ are as defined in the Summary of the Invention.

Within the above group Ia, a preferred group of compounds is that wherein $R^3$ is dicarboxyalkylaminocarbonylalkyl, preferably —CH$_2$CONHR or —C(CH$_3$)$_2$CONHR wherein R is dicarboxyalkyl, more preferably 1,2-dicarboxyethyl or 1,3-dicarboxyprop-2-yl, even more preferably (R)-1,2-dicarboxyethyl or (S)-1,2-dicarboxyethyl.

Within the above preferred group and more preferred groups contained therein, an even more preferred group of compounds is that wherein:

$R^z$ is halo, hydroxyalkyl, alkylsulfonylamino, alkylsulfonylaminoalkyl, alkylsulfonyl, aminosulfonyl, heterocycloalkylcarbonylalkyl, oxoheterocycloalkyl, carboxyalkyl, oxoheterocycloalkylalkyl, heteroaralkyl, ureido, alkylureido, dialkylureido, ureidoalkyl, alkylureidoalkyl, dialkylureidoalkyl, thioureido, thioureidoalkyl, —COR$^{12}$ (where R$^{12}$ is alkyl, hydroxyalkyl, or haloalkyl), -(alkylene)-COR$^{12}$ (where R$^{12}$ is alkyl or haloalkyl), —CONR$^{14}$R$^{15}$ (where R$^{14}$ is hydrogen or alkyl and R$^{15}$ is hydrogen, alkyl, aryl, aralkyl, heteroaryl, or heteroaralkyl), -(alkylene)-CONR$^{16}$R$^{17}$ (where R$^{16}$ is hydrogen or alkyl and R$^{17}$ is hydrogen, alkyl, hydroxyalkyl, aryl, aralkyl, heteroaryl, or heteroaralkyl), —NR$^{18}$R$^{19}$ (where R$^{18}$ is hydrogen or alkyl and R$^{19}$ is hydrogen, alkyl, acyl, aryl, aralkyl, heteroaryl, or heteroaralkyl), -(alkylene)-NR$^{20}$R$^{21}$ (where R$^{20}$ is hydrogen or alkyl and R$^{21}$ is hydrogen, alkyl, hydroxyalkyl, acyl, aryl, aralkyl, heteroaryl, or heteroaralkyl), —SO$_2$NR$^{22}$R$^{23}$(where R$^{22}$ and R$^{23}$ are independently alkyl), —NR$^{26}$SO$_2$NR$^{27}$ R$^{28}$ (where R$^{26}$ and R$^{27}$ are independently hydrogen or alkyl, and R$^{28}$ is hydrogen, alkyl, aryl, aralkyl, heteroaryl, or heteroaralkyl or R$^{27}$ and R$^{28}$ together with the nitrogen atom to which they are attached form heterocycloamino), or -(alkylene)-NR$^{29}$SO$_2$NR$^{30}$R$^{31}$ (where R$^{29}$ and R$^{30}$ are independently hydrogen or alkyl, and R$^{31}$ is hydrogen, alkyl, aryl, aralkyl, heteroaryl, or heteroaralkyl or R$^{30}$ and R$^{31}$ together with the nitrogen atom to which they are attached from heterocycloamino); or a zwitterion or a pharmaceutically acceptable salt thereof.

Preferably, R$^z$ is aminosulfonyl, alkylsulfonylaminoalkyl, halo, carboxyalkyl, hydroxyalkyl, heterocycloalkylcarbonylalkyl, ureido, ureidoalkyl, alkylureidoalkyl, dialkylureidoalkyl, —CONR$^{14}$R$^{15}$ (where R$^{14}$ is hydrogen or alkyl and R$^{15}$ is hydrogen or alkyl), -(alkylene)-CONR$^{16}$R$^{17}$ (where R$^{16}$ is hydrogen or alkyl and R$^{17}$ is hydrogen, alkyl, or hydroxyalkyl), or -(alkylene)-NR$^{20}$R$^{21}$ (where R$^{20}$ is hydrogen or alkyl and R$^{21}$ is hydrogen, alkyl, hydroxyalkyl or acyl).

More preferably, R$^z$ is fluoro, aminosulfonyl, ureidomethyl, tert-butylureidomethyl, 3,3-dimethylureidomethyl, aminomethyl, piperazin-1-ylcarbonyl-methyl, carboxymethyl, hydroxymethylcarbonylaminomethyl, aminocarbonyl, acetylaminomethyl, aminocarbonylmethyl, methylaminocarbonylmethyl, dimethylaminocarbonylmethyl, 2-hydroxyethylaminocarbonylmethyl, morpholin-4-yl-carbonylmethyl, methoxycarbonylaminomethyl, R or S, or RS-1-hydroxyethylcarbonyl-aminomethyl, hydroxymethyl, or methylsulfonylaminomethyl.

Within the above preferred group and more preferred, and even more preferred groups contained therein, a particularly preferred group of compounds is that wherein:

R$^{13}$ is hydrogen, hydroxy, methoxy, or ethoxycarbonyl, more preferably hydrogen. Most preferably, the compound of Formula I is represented by Formula Ib or Ic:

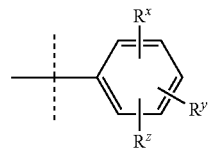

Ib

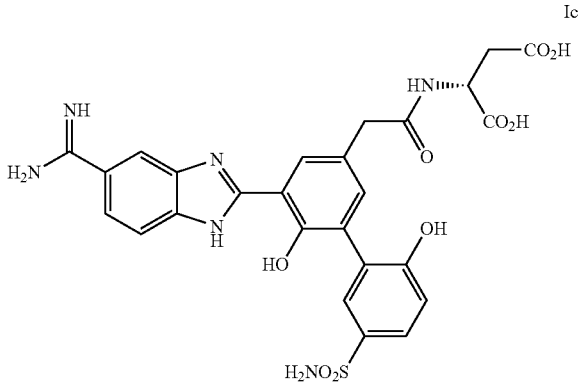

Ic or a zwitterion or a pharmaceutically acceptable salt thereof.
(II) Yet another preferred group of compounds of Formula I are those wherein the moiety:

is 3'-acetylphenyl, 3'-hydroxyphenyl, 2'-hydroxyphenyl, 3'-aminocarbonylphenyl, 3'-cyanophenyl, 5'-fluoro-2'-hydroxyphenyl, 5'-chloro-2'-hydroxyphenyl, 2'-hydroxy-methylphenyl, 2'-hydroxyphenyl, 5'-carboxy-2'-hydroxyphenyl, 2',5'-dihydroxyphenyl, 5'-cyano-2'-methoxyphenyl, 5'-aminocarbonyl-2'-methoxyphenyl, 2',6'-dihydroxyphenyl, 2'-hydroxy-5'-nitrophenyl, 2'-cyanophenyl, 3'-hydroxymethylphenyl, 5'-cyano-2'-hydroxy-phenyl, 5'-aminocarbonyl-2'-hydroxyphenyl, 2',6'-dihydroxyphenyl, 5'-aminomethyl-2'-hydroxyphenyl, 2'-hydroxy-5'-ureidomethylphenyl, 2'-hydroxy-5'-imidazol-2-ylphenyl, 5'-amino-2'-hydroxyphenyl, 2'-hydroxy-5'-ureidophenyl, 2'-hydroxy-5'-(2-morpholin-4-ylethyl)aminocarbonyl-phenyl, 3'-bromo-2'-hydroxy-5'-hydroxymethylphenyl, 5'-(2-cyanoethyl)-2'-hydroxyphenyl, 3'-bromo-5'-carboxymethyl-2'-hydroxyphenyl, 5'-(2-carboxyethyl)-2'-hydroxyphenyl, 5'-aminocarbonylmethyl-2'-hydroxyphenyl, 3',5'-dichloro-2'-hydroxyphenyl, 2'-hydroxy-5'-[2-(2-hydroxyethoxy)ethylaminocarbonyl]phenyl, 5'-dimethylaminosulfonylamino-2'-hydroxy-phenyl, 3'-bromo-5'-chloro-2'-hydroxy-phenyl, 2'-hydroxy-5'-(4-methylpiperazin-1-ylcarbonyl)phenyl, 2'-hydroxy-5'-(4-methylpiperazin-1-ylemthyl)phenyl, 5'-carbamimidoyl-2'-hydroxyphenyl, 5'-(2-dimethylaminoethylaminocarbonyl)-2'-hydroxyphenyl, or 5'-aminocarbonyl-2'-hydroxyphenyl. Preferably 2'-hydroxyphenyl, 5'-fluoro-2'-hydroxyphenyl, 5'-chloro-2'-hydroxyphenyl, 2'-hydroxymethylphenyl, 2'-hydroxyphenyl, 5'-carboxy-2'-hydroxy-phenyl, 2',5'-dihydroxyphenyl, 2',6'-dihydroxyphenyl, 2'-hydroxy-5'-nitrophenyl, 5'-cyano-2'-hydroxyphenyl, 5'-aminocarbonyl-2'-hydroxyphenyl, 2',6'-dihydroxyphenyl, 5'-aminomethyl-2'-hydroxyphenyl, 2'-hydroxy-5'-ureidomethylphenyl, 2'-hydroxy-5'-imidazol-2-ylphenyl, 5'-amino-2'-hydroxyphenyl, 2'-hydroxy-5'-ureidophenyl, 2'-hydroxy-5'-(2-morpholin-4-ylethyl)aminocarbonyl-phenyl, 3'-bromo-2'-hydroxy-5'-hydroxymethylphenyl, 5'-(2-cyanoethyl)-2'-hydroxyphenyl, 3'-bromo-5'-carboxymethyl-2'-hydroxyphenyl, 5'-(2-carboxyethyl)-2'-hydroxyphenyl, 5'-aminocarbonylmethyl-2'- hydroxyphenyl, 3',5'-dichloro-2'-hydroxyphenyl, 2'-hydroxy-5'-[2-(2-hydroxyethoxy)ethylaminocarbonyl]phenyl, 5'-dimethylaminosulfonylamino-2'-hydroxy-phenyl, 3'-bromo-5'-chloro-2'-hydroxyphenyl, 2'-hydroxy-5'-(4-methylpiperazin-1-ylcarbonyl)phenyl, 2'-hydroxy-5'-(4-methylpiperazin-1-ylmethyl)phenyl, 5'-carbamimidoyl-2'-hydroxyphenyl, 5'-methylaminocarbonylmethyl-2'-hydroxyphenyl, 5'-(2-dimethylaminoethylaminocarbonyl)-2'-hydroxyphenyl, or 5'-aminocarbonyl-2'-hydroxyphenyl. More preferably, 2',6'-dihydroxyphenyl, 5'-fluoro-2'-hydroxyphenyl, 3'-aminosulfonylphenyl, 5'-aminocarbonyl-2'-hydroxyphenyl, 5'-aminocarbonylmethyl-2'-hydroxyphenyl, 5'-methylaminocarbonylmethyl-2'-hydroxyphenyl, 5'-hydroxymethyl-2'-hydroxyphenyl, 5'-acetylaminomethyl-2'-hydroxyphenyl, 2'-hydroxy-5'-ureidophenyl; 2'-hydroxy-5'-ureidomethylphenyl, 2'-hydroxy-5'-N-methylureidomethylphenyl, 2'-hydroxy-5'-N,N-dimethylureidomethylphenyl, or 5'-methylsulfonylamino-2'-hydroxyphenyl.

Within this group, a more preferred group of compounds is that wherein $R^1$ and $R^2$ are hydrogen, $X^1$ is nitrogen, $X^2$-$X^4$ are carbon and $R^3$ is dicarboxyaminocarbonylalkyl, preferably —$CH_2CONHR$ or —$C(CH_3)_2CONHR$ wherein R is 1,2-dicarboxyethyl or 1,3-dicarboxyprop-2-yl, even more preferably (R)-1,2-dicarboxyethyl.

(III) Yet another preferred group of compounds of Formula I are those wherein the moiety:

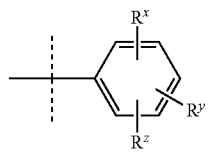

is a group of the formula:

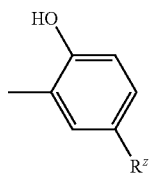

where $R^z$ is fluoro, aminosulfonyl, ureidomethyl, —$CH_2NHCONCH_3$, —$CH_2NHCONHC(CH_3)_3$, N,N-dimethylureidomethyl, aminomethyl, piperazin-1-ylcarbonylmethyl, carboxymethyl, —$CH_2NHCOCH_2OH$, aminocarbonyl, acetylaminomethyl, aminocarbonylmethyl, methylaminocarbonylmethyl, dimethylaminocarbonylmethyl, 2-hydroxyethylaminocarbonylmethyl, morpholin-4-ylcarbonylmethyl, methoxycarbonylaminomethyl, hydroxymethyl, or methylsulfonylaminomethyl.

Reference to the preferred embodiments set forth above is meant to include all combinations of particular and preferred groups unless stated otherwise.

General Synthetic Scheme

Compounds of this invention can be made by the methods depicted in the reaction schemes shown below.

The starting materials and reagents used in preparing these compounds are either available from commercial suppliers such as Aldrich Chemical Co., (Milwaukee, Wis.), Bachem (Torrance, Calif.), or Sigma (St. Louis, Mo.) or are prepared by methods known to those skilled in the art following procedures set forth in references such as Fieser and Fieser's Reagents for Organic Synthesis, Volumes 1-17 (John Wiley and Sons, 1991); Rodd's Chemistry of Carbon Compounds, Volumes 1-5 and Supplementals (Elsevier Science Publishers, 1989); Organic Reactions, Volumes 1-40 (John Wiley and Sons, 1991), March's Advanced Organic Chemistry, (John Wiley and Sons, 4th Edition) and Larock's Comprehensive Organic Transformations (VCH Publishers Inc., 1989). These schemes are merely illustrative of some methods by which the compounds of this invention can be synthesized, and various modifications to these schemes can be made and will be suggested to one skilled in the art having referred to this disclosure.

The starting materials and the intermediates of the reaction may be isolated and purified if desired using conventional techniques, including but not limited to filtration, distillation, crystallization, chromatography and the like. Such materials may be characterized using conventional means, including physical constants and spectral data.

Unless specified to the contrary, the reactions described herein take place at atmospheric pressure over a temperature range from about −78° C. to about 150° C., more preferably from about 0° C. to about 125° C. and most preferably at about room (or ambient) temperature, e.g., about 20° C.

Compounds of Formula I in which $X^1$ is —N—, $R^{13}$ is hydrogen, $R^3$ is dicarboxyalkylaminocarbonylalkyl, and $X^2$, $X^3$, $X^4$, $R^1$, $R^2$, $R^x$, $R^y$, and $R^z$ are as defined in the Summary of the Invention can be prepared as described in Scheme I below.

Scheme I

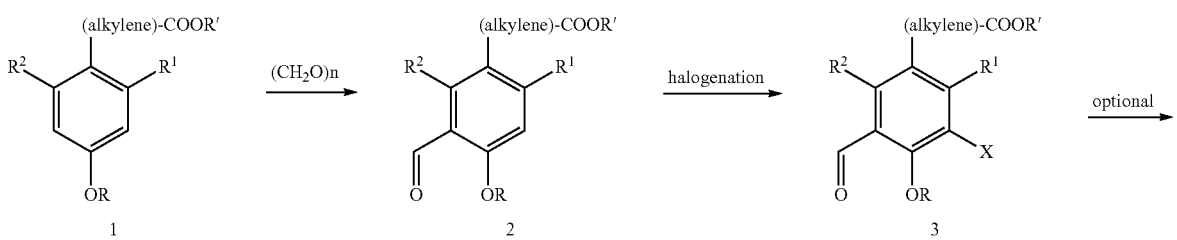

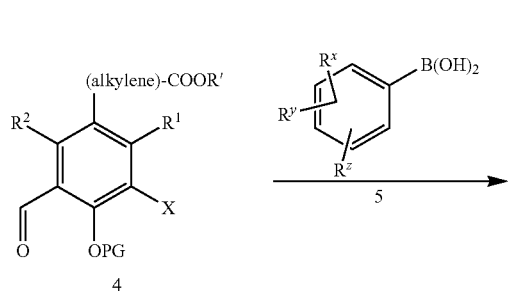
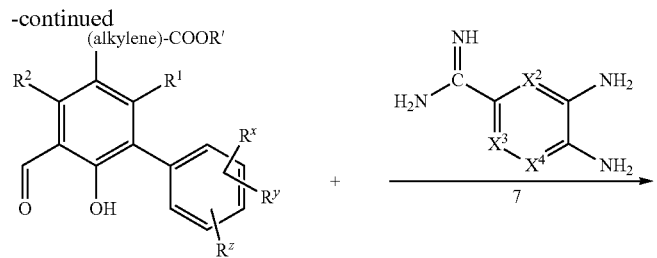
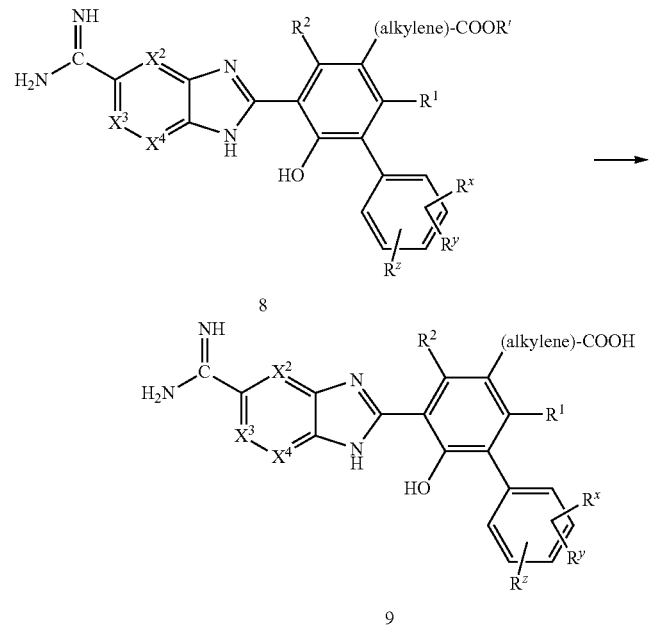

Formylation of a phenol derivative of formula 1 (where R is hydrogen or hydroxy protecting group, preferably hydroxy, and R' is alkyl) provides a compound of formula 2. The formylation reaction is carried out in the presence of magnesium chloride and an organic base such as triethylamine, and the like, and in a suitable organic solvent such as acetonitrile, and the like. Halogenation of 2 with a suitable halogenating agent such as N-bromosuccinimide, N-iodosuccinimide, and the like and in a suitable organic solvent such as dimethylformamide, and the like provides a compound of formula 3 where X is halo.

Compounds of formula 1 are either commercially available or they can be prepared by methods well known in the art. For example, methyl 4-hydroxyphenyl-acetate is commercially available.

Protection of the hydroxy group in 3 (where R is hydrogen) with a suitable hydroxy protecting group such as alkyl, methyoxyethoxymethyl, benzyl, and the like, provides a compound of formula 4. A comprehensive list of other suitable hydroxy protective groups can be found in T. W. Greene, *Protective Groups in Organic Synthesis*, John Wiley & Sons, Inc. 1999, the disclosure of which is incorporated herein by reference in its entirety. Preferred hydroxy protecting groups are 2-methoxyethoxymethyl and benzyl. The reaction is typically carried out in the presence of a base such as diisopropylethylamine, and the like, and in a halogenated organic solvent such as dichloromethane, carbon tetrachloride, chloroform, and the like.

Treatment of 5 with a boronic acid compound of formula 5 where $R^x$, $R^y$ and $R^z$ are as defined in the Summary of the Invention, or a protected derivative thereof, provides a biphenyl compound of formula 6. The reaction is carried out in the presence of a palladium catalyst such as tetrakis(triphenylphosphine)palladium and in a suitable organic solvent such as toluene or dimethoxyethane and a base such as aqueous sodium carbonate, potassium carbonate and the like. Alternatively, the reaction can be carried out in the presence of $PdCl_2(dppf).CH_2Cl_2$ complex in the presence of diisopropylamine in a suitable organic solvent such as tetrahydrofuran, and the like. Compounds of formula 5 are either commercially available or they can be prepared by methods well known in the art. For example, 5-fluoro-2-methoxyboronic acid is commercially available. Others can be prepared by treating a halogenated benzene of the formula Ph-($R^x$, $R^yR^z$)X where X is halo and $R^x$, $R^y$ and $R^z$ are as defined in the Summary of the Invention with organic metallic reagent such as n-butyl lithium to generate a organic metallic species which upon treatment with trimethylborate provides the corresponding boronic acid. Halogenated benzene of the formula Ph-($R^x$, $R^yR^z$)X is either commercially available or it can be prepared by methods well known in the art. For example, 2-bromo-4-fluorophenol is commercially available. 1-(3-Bromo-4-methoxyethoxymethoxybenzyl)-3-tert-butyl urea can be prepared by treating 3-bromo-4-hydroxybenzonitrile with methoxyethoxymethyl chloride in the presence of a base such as diisopropylamine, and the like, followed by reduction of the resulting 3-bromo-4-methylethoxymethoxy) benzonitrile to 3-bromo-4-methoxyethoxymethoxybenzylamine with a suitable reducing agent such as diborane. Treatment of 3-bromo-4-methylethoxybenzylamine with tert-butylisocyanate then provides the desired compound. 1-(3-Bromo-4-methoxyethoxymethoxybenzyl)-3-tert-butyl urea can be converted to 1-(3-bromo-4-methoxyethoxymethoxybenzyl)urea by removal of the tert-butyl group under acidic hydrolysis reaction conditions.

Condensation of 6 with a 1,2-diamino compound of formula 7 in the presence of a suitable oxidant such as benzoquinone, air oxidation, or $FeCl_3$ and $O_2$ and in a suitable organic solvent such as methanol, ethanol, and the like, provides a compound of formula 8 which upon removal of the R' group under basic hydrolysis reaction conditions provides a compound of formula 9. Alternatively, the reaction is carried out utilizing aqueous solution of sodium metabisulfite in an alcoholic solvent such as isopropanol, and in the presence of oxygen.

Reaction of 9 with dicarboxy-protected dicarboxyalkylamino provides a dicarboxy-protected compound of Formula I which upon removal of the dicarboxy protecting groups provides a compound of Formula I where $X^1$ is —N—. The amination reaction is carried out reacting in the presence of a suitable coupling agent e.g., benzotriazole-1-yloxytris-pyrrolidinophosphonium hexafluorophosphate (PyBOP®), O-benzotriazol-1-yl-N,N,N',N'-tetramethyl-uronium hexafluorophosphate (HBTU), O-(7-azabenzotriazol-1-yl)-1,1,3,3-tetramethyluronium hexafluorophosphate (HATU), 1-(3-dimethylaminopropyl)-3-ethylcarbodiimide hydrochloride (EDC), or 1,3-dicyclohexylcarbodiimide (DCC), optionally in the presence of 1-hydroxybenzotriazole (HOBT), and a base such as N,N-diisopropylethylamine, triethylamine, N-methylmorpholine, and the like. The reaction is typically carried out at 20 to 30° C., preferably at about 25° C., and requires 2 to 24 h to complete. Suitable reaction solvents are inert organic solvents such as N,N-dimethylformamide, and the like.

Other methods of preparing compounds of Formula (I) are disclosed in U.S. Patent Application Hu, Huiyong et al., Publication No. 20030114457 A1 published on Jun. 19, 2003, the disclosure of which is incorporated herein by reference in its entirety.

Compounds of Formula I in which $X^1$ is —CH—, $R^{13}$ is hydrogen, $R^3$ is dicarboxyalkylaminocarbonylalkyl, and $X^2$, $X^3$, $X^4$, $R^1$, $R^2$, $R^x$, $R^y$, and $R^z$ are as defined in the Summary of the Invention can be prepared as described in Scheme II below.

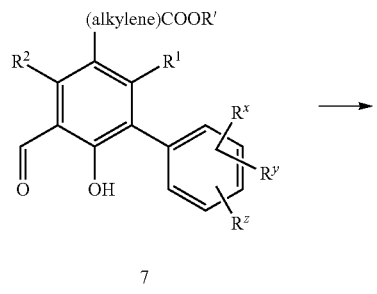

Scheme II

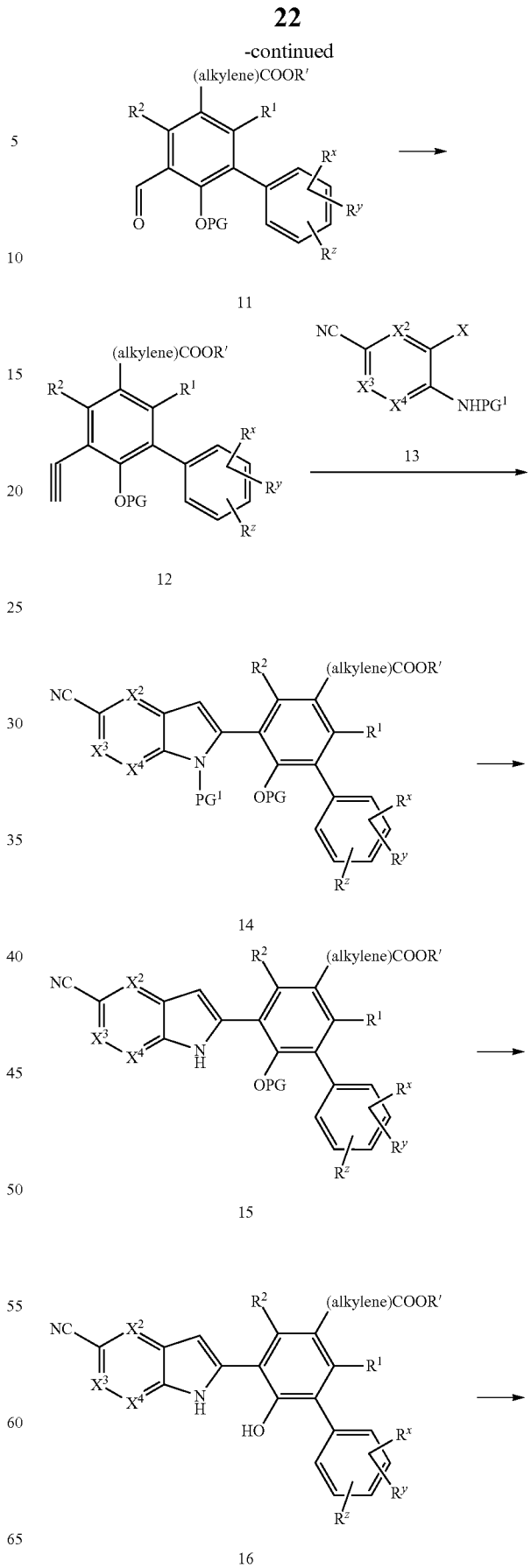

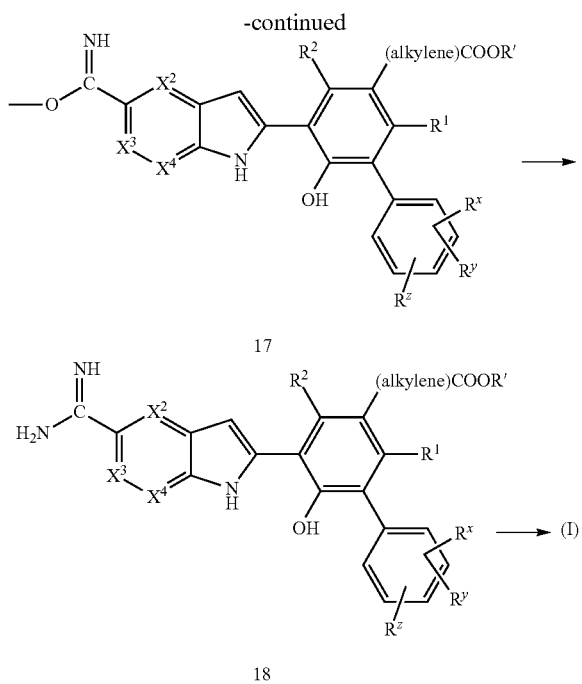

Protection of the hydroxy group in a compound of formula 7 with a suitable hydroxy protecting group provides a compound of formula 11. A comprehensive list of suitable hydroxy protective groups can be found in T. W. Greene, *Protective Groups in Organic Synthesis*, John Wiley & Sons, Inc. 1999, the disclosure of which is incorporated herein by reference in its entirety. Preferred hydroxy protecting group is 2-methoxyethoxymethyl. The reaction is typically carried out in the presence of a base such as N,N-diisopropylethylamine, and the like, and in a halogenated organic solvent such as dichloromethane, carbon tetrachloride, chloroform, and the like.

Ethynylation of 11 utilizing a modified procedure described in Muller, S.; Liepold, B.; Roth G. J.; Bestmann H. J. *Synlett* 1996, 6, 521-522 provides a ethynylbiphenyl compound of formula 12.

Reaction of a compound of formula 12 with a cyano compound of formula 13 where $PG^1$ is a suitable nitrogen protecting group such as methylsulfonyl, tert-butoxycarbonyl, trifluoroacetyl, and the like, and X is halo, utilizing the reaction conditions described in Sakamoto, T; Kondo, Y.; Iwashita, S.; Nagano, T.; Yamanaka, H. *Chem. Pharm. Bull.* 1988, 36, 1305 provides 5-cyano-2-biphenyl-3-ylindole compound of formula 14 (where $X^1$, $X^2$, $X^3$ and $X^4$ are carbon and $PG^1$ is not hydrogen). Deprotection of the amino group in 14 provides a 5-cyano-2-(biphenyl-3-yl)-1H-indole compound of formula 15. The reaction conditions utilized in the deprotection step depends on the nature of the nitrogen protecting group. For example, if the protecting group is methylsulfonyl it is removed under basic hydrolysis reaction conditions. Suitable bases are aqueous sodium hydroxide, potassium hydroxide, and the like. The reaction is carried out in an alcoholic solution such as methanol, ethanol, and the like. If the protecting group is tert-butoxycarbonyl it is removed under acidic hydrolysis reaction conditions. Compounds of formula 13 are either commercially available or they can be prepared by methods well known in the art.

The hydroxy-protecting group in 15 is then removed to provide 5-cyano-2-(2-hydroxybiphenyl-3-yl)-1H-indole 16. The reaction conditions employed for the deprotection reaction depend on the nature of the hydroxy protecting group. For example, if the protecting group is 2-methoxyethoxymethyl, it is removed by treating 16 with an acid under non-aqueous reaction conditions, in a suitable alcoholic solvent.

The cyano group in compound 16 is then converted into the carbamimidoyl group by first treating 16 with hydrogen chloride gas in an anhydrous alcoholic solvent such as methanol, ethanol and the like, and then treating the resulting (5-methoxycarbonimidolyl)-2-(2-hydroxybiphenyl-3-yl)-1H-indole 17 with an inorganic base such as ammonium carbonate, and the like in an alcoholic solvent such as methanol, ethanol, or with excess ammonia to give resulting (5-carbamimidolyl)-2-(2-hydroxybiphenyl-3-yl)-1H-indole of formula 18 which is then converted to a compound of Formula I as described in Scheme I above.

Compounds of Formula I can be converted to other compounds of Formula I. For example, a compound of Formula I where $R^x$ is alkoxy, can be converted to corresponding compound of Formula I where $R^x$ is hydroxy by hydrolysis of the alkoxy group by a suitable dealkylating reagent such as hydrobromic acid, and the like. A compound of Formula I where $R^z$ is cyano can be converted to a corresponding compound of Formula I where $R^z$ is aminocarbonyl under hydrolysis reaction conditions. The cyano group can also be reduced to give aminomethyl group which can be treated with isocyanate or thiocyanate to give corresponding compound of Formula I where $R^z$ is ureidomethyl or thioureidomethyl respectively. A compound of Formula I where $R^{13}$ is hydrogen can be converted to a corresponding compound of Formula I where $R^{13}$ is hydroxy or alkoxy by reacting it with hydroxylamine or alkoxyamine under conditions well known in the art.

Utility

The compounds of this invention inhibit Factors VIIa, IXa, Xa, and XIa, in particular Factor VIIa, and are therefore useful as anticoagulants for the treatment or prevention of thromboembolic disorders in mammals.

Particular disease states which may be mentioned include the therapeutic and/or prophylactic treatment of venous thrombosis (e.g. DVT) and pulmonary embolism, arterial thrombosis (e.g. in myocardial infarction, unstable angina, thrombosis-based stroke and peripheral arterial thrombosis), and systemic embolism usually from the atrium during atrial fibrillation or from the left ventricle after transmural myocardial infarction, or caused by congestive heart failure; prophylaxis of reocclusion (i.e., thrombosis) after thrombolysis, percutaneous trans-luminal angioplasty (PTA) and coronary bypass operations; the prevention of rethrombosis after microsurgery and vascular surgery in general.

Further indications include the therapeutic and/or prophylactic treatment of disseminated intravascular coagulation caused by bacteria, multiple trauma, intoxication or any other mechanism; anticoagulant treatment when blood is in contact with foreign surfaces in the body such as vascular grafts, vascular stents, vascular catheters, mechanical and biological prosthetic valves or any other medical device; and anticoagulant treatment when blood is in contact with medical devices outside the body such as during cardiovascular surgery using a heart-lung machine or in haemodialysis; the therapeutic and/or prophylactic treatment of idiopathic and adult respiratory distress syndrome, pulmonary fibrosis following treatment with radiation or chemotherapy, septic shock, septicemia, inflammatory responses, which include, but are not limited to, edema, acute or chronic atherosclerosis such as coronary arterial disease and the formation of atherosclerotic plaques, cerebral arterial disease, cerebral infarction, cerebral thrombosis, cerebral embolism, peripheral arterial disease, ischaemia, angina (including unstable angina), reperfusion damage, restenosis after percutaneous trans-luminal angioplasty (PTA) and coronary artery bypass surgery.

The compounds of Formula I can also be used in the treatment of cancer or rheumatoid arthritis.

Testing

The ability of the compounds of this invention to inhibit factor VIIa and Xa can be tested in vitro and in vivo assays described in biological assays Example 1 and 2 below.

Administration and Pharmaceutical Compositions

In general, the compounds of this invention will be administered in a therapeutically effective amount by any of the accepted modes of administration for agents that serve similar utilities. The actual amount of the compound of this invention, i.e., the active ingredient, will depend upon numerous factors such as the severity of the disease to be treated, the age and relative health of the subject, the potency of the compound used, the route and form of administration, and other factors.

Therapeutically effective amounts of compounds of Formula I may range from approximately 0.01-50 mg per kilogram body weight of the recipient per day; preferably about 0.1-20 mg/kg/day, even more preferably about 0.25 mg/kg/day to 10 mg/kg/day. Thus, for administration to a 70 kg person, the dosage range would most preferably be about 7 mg to 1.4 g per day.

In general, compounds of this invention will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral or parenteral using a convenient daily dosage regimen, which can be adjusted according to the degree of affliction. Oral compositions can take the form of tablets, pills, capsules, semisolids, powders, sustained release formulations, solutions, suspensions, elixirs, aerosols, or any other appropriate compositions.

The choice of formulation depends on various factors such as the mode of drug administration (e.g., for oral administration, formulations in the form of tablets, pills or capsules are preferred) and the bioavailability of the drug substance. Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of Formula I in combination with at least one pharmaceutically acceptable excipient. Acceptable excipients are non-toxic, aid administration, and do not adversely affect the therapeutic benefit of the compound of Formula I. Such excipient may be any solid, liquid, semi-solid or, in the case of an aerosol composition, gaseous excipient that is generally available to one skilled in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of this invention in aerosol form. Inert gases suitable for this purpose are nitrogen, carbon dioxide, etc.

Other suitable pharmaceutical excipients and their formulations are described in Remington's Pharmaceutical Sciences, edited by E. W. Martin (Mack Publishing Company, 18th ed., 1990).

The amount of the compound in a formulation can vary within the full range employed by those skilled in the art. Typically, the formulation will contain, on a weight percent (wt %) basis, from about 0.01-99.99 wt % of a compound of Formula I based on the total formulation, with the balance being one or more suitable pharmaceutical excipients. Preferably, the compound is present at a level of about 1-80 wt %. Representative pharmaceutical formulations containing a compound of Formula I are described below.

The compounds of Formula I can be administered alone or in combination with other compounds of Formula I or in combination with one or more other active ingredient(s). For example, a compound of Formula I can be administered in combination with another anticoagulant agent(s) independently selected from a group consisting of a thrombin inhibitor, a factor IXa, and a factor Xa inhibitor. Preferably, the thrombin inhibitor is Inogatran®, Melagatran® or prodrugs thereof which are disclosed in PCT Application Publication Nos. WO 94/29336 and WO 97/23499, the disclosures of which are incorporated herein by reference in their entirety. Factor Xa inhibitors that may be used in the combination products according to the invention include those described in *Current Opinion in Therapeutic Patents*, 1993, 1173-1179 and in international patent applications WO 00/20416, WO 00/12479, WO 00/09480, WO 00/08005, WO 99/64392, WO 99/62904, WO 99/57096, WO 99/52895, WO 99/50263, WO 99/50257, WO 99/50255, WO 99/50254, WO 99/48870, WO 99/47503, WO 99/42462, WO 99/42439, WO 99/40075, WO 99/37304, WO 99/36428, WO 99/33805, WO 99/33800, WO 99/32477, WO 99/32454, WO 99/31092, WO 99/26941, WO 99/26933, WO 99/26932, WO 99/26919, WO 99/26918, WO 99/25720, WO 99/16751, WO 99/16747, WO 99/12935, WO 99/12903, WO 99/11658, WO 99/11617, WO 99/10316, WO 99/07732, WO 9/07731, WO 99/05124, WO 99/00356, WO 99/00128, WO 99/00127, WO 99/00126, WO 9/00121, WO 98/57951, WO 98/57937, WO 98/57934, WO 98/54164, WO 98/46591, WO 98/31661, WO 98/28282, WO 98/28269, WO 98/25611, WO 98/24784, WO 98/22483, WO 98/16547, WO 98/16525, WO 98/16524, WO 98/16523, WO 98/15547, WO 98/11094, WO 98/07725, WO 98/06694, WO 98/01428, WO 7/48706, WO 97/46576, WO 97/46523, WO 97/38984, WO 97/30971, WO 97/30073, WO 97/29067, WO 97/24118, WO 97/23212, WO 97/21437, WO 97/08165, WO 97/05161, WO 96/40744, WO 96/40743, WO 96/40679, WO 96/40100, WO 96/38421, WO 96/28427, WO 96/19493, WO 96/16940, WO 95/28420, WO 94/13693, WO 00/24718, WO 99/55355, WO 99/51571, WO 99/40072, WO 99/26926, WO 98/51684, WO 97/48706, WO 97/24135, WO 97/11693, WO 00/01704, WO 00/71493, WO 00/71507, WO 00/71508, WO 00/71509, WO 00/71511, WO 00/71512, WO 00/71515, WO 00/71516, WO 00/13707, WO 00/31068, WO 00/32590, WO 00/33844, WO 00/35859, WO 00/35886, WO 00/38683, WO 00/39087, WO 00/39092, WO 00/39102, WO 00/39108, WO 00/39111, WO 00/39117, WO 00/39118, WO 00/39131, WO 00/40548, WO 00/40571, WO 00/40583, WO 00/40601, WO 00/47207, WO 00/47553, WO 00/47554, WO 00/47563, WO 00/47578, WO 00/51989, WO 00/53264, WO 00/59876, WO 00/59902, WO 00/71510, WO 00/76970, WO 00/76971, WO 00/78747, WO 01/02356, WO 01/02397, WO 01/05784, WO 01/09093, WO 01/12600, WO 01/19788, WO 01/19795, WO 01/19798, WO 93/15756, WO 94/17817, WO 95/29189, WO 96/18644, WO 96/20689, WO 96/39380, WO 97/22712, WO 97/36580, WO 97/36865, WO 97/48687, WO 98/09987, WO 98/46626, WO 98/46627, WO 98/46628, WO 98/54132, WO 99/07730, WO 99/33458, WO 99/37643 and WO 99/64446; in U.S. Pat. Nos. 6,034,093, 6,020,357, 5,994,375, 5,886,191, 5,849,519, 5,783,421, 5,731,315, 5,721,214, 5,693,641, 5,633,381, 5,612,378, 6,034,127, 5,670,479, 5,658,939, 5,658,930, 5,656,645, 5,656,600, 5,639,739, 5,741,819, 6,057,342, 6,060,491, 6,080,767, 6,087,487, 6,140,351, 6,395,731, and 5,646,165; in Japanese patent applications Nos. JP 99152269, JP 10017549, JP 10001467, JP 98017549, JP 00178243, JP 11140040, JP 12143623, JP 12204081, JP 12302765, JP 6327488 and JP 98001467; in European patent applications EP 937 723, EP 937 711, EP 874 629, EP 842 941, EP 728 758, EP 540 051, EP 419 099, EP 686 642, EP 1 016 663 and EP 529 715; and in German patent applications Nos. DE 19845153, DE 19835950, DE 19743435, DE 19829964, DE 19834751, DE 19839499, DE19900355, DE19900471 and DE 19530996, the specific and generic disclosures in all of which documents are hereby incorporated by reference.

Factor Xa inhibitors also include those disclosed in international patent applications WO 96/10022, WO 97/28129, WO 97/29104, WO 98/21188, WO 99/06371, WO 99/57099, WO 99/57112, WO 00/47573, WO 00/78749, WO 99/09027 and WO 99/57113, the specific and generic disclosures in all of which documents are hereby incorporated by reference, as well as 4-{4-[4-(5-chloroindol-2-ylsulfonyl)piperazine-1-carbonyl]phenyl}-pyridine-1-oxide and pharmaceutically acceptable derivatives thereof. Preferred Factor Xa inhibitors include antistatin, tick anticoagulant protein and those known as SQ-311 and SQ-315 (see international patent application WO 98/57951); SN-292 (see international patent application WO 98/28282); SN-429 and SN 116 (see international patent application WO 98/28269); RPR-208707 (see international patent application WO 98/25611 at Example 48); XU-817 (see international patent application WO 98/01428); SF-324 and SF-303 (see international patent application WO 97/23212); YM 60828 (see international patent application WO 96/16940 at Example 75); FACTOREX (see U.S. Pat. No. 5,783,421); SF-324 (see European patent application EP 874 629); DX9065A (see European patent application EP 540 051 at Example 39); 1-(4-carbamimidoylbenzyl)-4-(6-chloronaphthalene-2-ylsulfonyl)-piperazin-2-one (see JP 12204081 at Example 2); M55555 (see international patent application WO 99/33805 at Example 39); DPC423 (1-(3-carbamimidoylphenyl)-2-(2'-aminolsulfonyl[1,1'-biphenyl]-4-ylaminocarbonyl)-4-bromopyrrole, see international patent application WO 98/28269); 3-(3,5-difluoro-6-[3-(4,5dihydro-1-methyl-imidazol-2-yl)-phenoxy]-4-[2,3-dihydroxy-propoxy]-pyridin-2-yloxy)-4-hydroxy-benzamidine (see international patent application WO 00/31068); ZK-807834 (see international patent application WO 7/29067); 1,4-diaza-4-(6-chloronaphthalene-2-ylsulfonyl)-6-(methoxymethyl)-7-oxa-1'-(pyridin-4-yl)spiro[bicyclo-[4-3.0]-nonane-8,4'-piperidine]-2-one (see international patent application WO 01/02397); (S)-1-(4-aminoquinazolin-7-ylmethyl)-4-[2-(5-chlorothien-2-yloxy)acetyl]-3-methoxymethylpiperazin-2-one (see international patent application WO 00/32590); 3-(2-[4-(2-aminosulfonyl-phenyl)benzoylphenoxy)-benzamidine (see international patent application WO 01/19788); and 4-(2-[4-(5-chloroindol-2-yl-sulfonyl)-2-(pyrrolidin-1-ylcarbonylmethyl)piperazin-1-ylcarbonyl]-thiazol-5-yl)pyridine N-oxide (see Japanese patent application No. JP 12143623); as well as the compounds of Example 7 of international patent application WO 98/21188, of Examples 3 and 6 of WO 99/57113, of Example 6 of international patent application WO 00/78747, of Examples 188, 211 and 167 of U.S. Pat. No. 6,080,767, of Examples 40, 54 and 55 of international patent application WO 99/33805, of Examples 5, 6, 8, 9, 10, 11, 12, 13, 15, 16 and 17 of international patent application WO 01/05784, of Examples 6, 7, 8, 9, 10, 11, 12, 13, 14, 15, 16, 17, 22, 23, 25, 26, 28, 29, 30, 31, 32, 33, 34, 38, 39, 40, 41, 42 and 43 of international patent application WO 01/12600, and of Examples 802 and 877 of international patent application WO 00/35886. Other anticoagulant agents that can be used in the combination therapy are those disclosed in U.S. Patent Applications Publication Nos. 20020065303, 20020061842, 20020058677, 20020058657, 20020055522, 20020055469, 20020052368, 20020040144, 20020035109, 20020032223, 20020028820, 20020025963, 20020019395, 20020019394, 20020016326, 20020013314, 20020002183, 20010046974, 20010044537, 20010044536, 20010025108, 20010023292, 20010023291, 20010021775, 20010020020033, 20010018423, 20010018414, and 20010000179, which are incorporated herein by reference in their entirety.

Suitable formulations for use in administering melagatran and derivatives (including prodrugs) thereof are described in the literature, for example as described in inter alia international patent applications WO 94/29336, WO 96/14084, WO 96/16671, WO 97/23499, WO 97/39770, WO 97/45138, WO 98/16252, WO 99/27912, WO 99/27913, WO 00/12043 and WO 00/13671, the disclosures in which documents are hereby incorporated by reference.

Similarly, suitable formulations for use in administering Factor Xa inhibitors and derivatives (including prodrugs) thereof are described in the literature, for example as described in the prior art documents relating to Factor Xa inhibitors that are mentioned hereinbefore, the disclosures in which documents are hereby incorporated by reference. Otherwise, the preparation of suitable formulations, and in particular combined preparations including both melagatran/derivative and Factor Xa inhibitor/derivative may be achieved non-inventively by the skilled person using routine techniques. The amounts of melagatran, Factor Xa inhibitor, or derivative of either, in the respective formulation(s) will depend on the severity of the condition, and on the patient to be treated, as well as the compound(s) which is/are employed, but may be determined non-inventively by the skilled person.

Suitable doses of melagatran, Factor Xa inhibitors and derivatives of either, in the therapeutic and/or prophylactic treatment of mammalian, especially human, patients may be determined routinely by the medical practitioner or other skilled person, and include the respective doses discussed in the prior art documents relating to melagatran (or derivatives (including prodrugs) thereof), and to Factor Xa inhibitors, that are mentioned hereinbefore, the disclosures in which documents are hereby incorporated by reference.

EXAMPLES

All solvents and reagents were purchased from Aldrich and used as received except where noted. All reactions and products were analyzed using HPLC, employing an Agilent HP1100 system fitted with a diode array detector and a Phenomenex Prodigy 5μ ODS-3 100A column, 150 mm×3.0 mm ID [Phenomenex catalogue #00D4096-Y0]. Chromatographic runs were performed at column temperatures of 40° C. and compound detection was performed at both 214 and 254 nm. Gradient elution was employed, using acetonitrile-water mobile phase systems with TFA as acid buffer, typically over 5-10 minute gradients. Moisture content of reaction products and reagents were determined using an EM-Science model V-200 AQUASTAR volumetric Karl Fischer titrator. Combustion analyses were performed by Robertson Microlit Laboratories, Inc., Madison, N.J.

Reference A

Synthesis of methyl(3-bromo-5-formyl-4-hydroxyphenyl)acetate

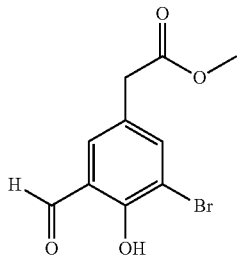

Method A
Step 1

To a 12 L round bottom flask with overhead stirrer, condenser, thermocouple, and heating mantle was added methyl 4-hydroxyphenylacetate (302 g, 1.82 mol) and acetonitrile (3 L). The reaction mixture was stirred until the solids had dissolved, then triethylamine (1015 mL, 737 g, 7.28 mol) was added. Anhydrous magnesium chloride (346 g, 3.63 mol) was then added in portions over a 5-minute period, resulting in an increase in the internal temperature to ~55° C. The reaction mixture was heated to reflux (internal temperature: 68° C.) for 1 h, resulting in a brownish solution with some suspended white solids. Paraformaldehyde (382 g, 12.7 mol, Aldrich catalogue number 44,124-4) was added and the heating was continued for 16-24 h until HPLC-UV analysis shows >95% consumption of methyl 4-hydroxyphenylacetate. The reaction mixture was diluted with diethyl ether (3 L), and 1N aqueous HCl (3 L) was added, resulting in dissolution of the magnesium salts. The layers were separated and the organic phase was washed with 1N aqueous HCl, followed by saturated aqueous sodium chloride. The organic was dried ($Na_2SO_4$) and concentrated to give (3-formyl-4-hydroxyphenyl)acetic acid methyl ester (308 g; 87.3%) as an amber oil.
Step 2

To a 2 L round bottom flask with magnetic stirrer, thermocouple, and ice water bath was added (3-formyl-4-hydroxyphenyl)acetic acid methyl ester (308 g, 1.59 mol) and N,N-dimethylformamide (1 L). The reaction mixture was stirred and cooled to −5 to 5° C. A solution of N-bromosuccinimide (311 g, 1.75 mol) in DMF (1.5 to 2 L) was added dropwise, at such a rate to keep the internal temperature between 5 and 10° C. Once the addition was complete, the reaction mixture was allowed to warm to room temperature and monitored for completion by HPLC analysis. The reaction time was about 4 h. The reaction mixture was diluted with isopropylacetate (3 L), and the resulting solution was extracted with water to remove the DMF. Concentration of the organic phase afforded a reddish solid that was dissolved in hot isopropanol (400 mL) and allowed to cool while stirring. The resulting off-white crystalline product was filtered and washed with cold IPA (~20° C.; 400 mL) to yield methyl (3-bromo-5-formyl-4-hydroxyphenyl)acetate (368 g, 84.7%) as off-white crystals.

Method B: Alternative Method for the Synthesis of methyl (3-bromo-5-formyl-4-hydroxyphenyl)-acetate
Step 1

A 3-neck, 3 L round-bottom flask equipped with an overhead stirrer, thermometer, reflux condensor, and $N_2$ line was charged with (4-hydroxyphenyl)-acetic acid methyl ester (Aldrich; 166.2 g, 1.00 mol) and acetonitrile (1000 mL). Triethylamine (121.4 g, 1.20 mols, 1.2 eq.) was added in a single portion to the stirring solution and then magnesium chloride (98% w/w; 115.2 g, 1.10 mols, 1.1 eq.) was added portionwise over 15 min. The reaction mixture was stirred for 20 min. and then heated to 75° C. for 1 h during which the magnesium salts dissolved. Paraformaldehyde (95% w/w as prills; Aldrich #44,124-4; 63.2 g, 2.00 mols, 2.00 eq.) was added portionwise over 30 min. After heating to 80° C. for 2 h, the reaction was found to be incomplete and hence a further portion of paraformaldehye (6.00 g, 0.20 mols, 0.2 eq.) was added portion-wise. After 2 h, the reaction mixture was concentrated in situ ($T_{int}$≦70° C.; approx. 30-40 Torr) to approx. ⅓ its original volume and then allowed to cool to room temperature. Water (500 mL) was added over a few minutes and a thick yellow slurry formed. Upon returning to ~30° C. conc. phosphoric acid (85% w/w; 230.7 g, 2.00 mols) was added portion-wise and the mixture was stirred vigorously. Most of the solids dissolved and after cooling ($T_{int}$~20° C.) isopropyl acetate (500 mL) was added in a single portion. The mixture was stirred vigorously until all the solids dissolved and the layers separated cleanly. The solution was transferred to a separating funnel and the aqueous layer was separated. The organic layer was washed with a mixture of water and conc. phosphoric acid (115 g, 1.00 mol) and the organic layer containing a mixture of methyl 3-formyl-4-hydroxyphenylacetate and methyl 4-hydroxyphenylacetate was separated and used in the next step.
Step 2

The solution containing a mixture of methyl 3-formyl-4-hydroxyphenylacetate and methyl 4-hydroxyphenylacetate (~900 mL total volume, containing 500 mL ispropyl acetate with ~300 mL acetonitrile) was transferred back to the original reaction vessel and acetonitrile (900 mL) added. The reaction was stirred and heated to 60° C. and a mixture of sodium hydrogensulfite ($NaHSO_3$; Aldrich #24, 397-3, 58.5% $SO_2$; 109.4 g, 1.00 mols) dissolved in water (175 mL) was added in a single portion to the stirring reaction and heating was continued. Within 5 min, a white precipitate formed. After 16 h, the reaction mixture was allowed to cool gradually to $T_{int}$: ~5° C. The precipitates were collected and the filter cake washed with cold 1:1 acetonitrile-isopropyl acetate and dried to give sodium salt of 4-hydroxy-3-(hydroxysulfomethyl)phenyl]-acetic acid methyl ester (208 g, 70%).
Step 3

Sodium salt of 4-hydroxy-3-(hydroxysulfomethyl)phenyl]-acetic acid methyl ester (205.2 g, 0.688 mol) was dissolved in water (2 L) at room temperature and stirred. Conc. phosphoric acid (400 mL) was added in a single portion and the mixture turned cloudy within minutes. The reaction mixture was extracted with dichloromethane and the combined extracts were concentrated to yield methyl (3-formyl-4-hydroxyphenyl)acetate (112 g, 58%) which was converted to the title compound as described in Method A, Step 2 above.

Reference B

Synthesis of 3,4-diaminobenzamidine monohydrochloride

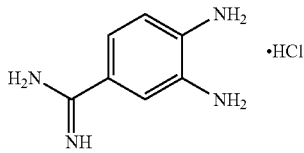 [SMILES: N=C(N)c1ccc(N)c(N)c1 ; Cl]

Step 1

A mixture of 4-amino-3-nitrobenzonitrile (63.3 g, 388 mmol) in 1,4-dioxane (600 mL) and anhydrous ethanol (600 mL) was cooled in an ice water bath to 0-5° C. and treated with gaseous HCl for 1.5 h. The reaction mixture was tightly sealed and allowed to warm up to room temperature with stirring for 18 h. The flask was then carefully unsealed and the reaction mixture was diluted with anhydrous diethyl ether (about 2.4 L) until a cloudy solution was obtained. A minimum amount of absolute ethanol required to give a clear solution was then added, and the resulting solution stirred until crystals of 4-amino-3-nitro-benzimidic acid ethyl ester were observed. Ether was then cautiously added to complete the crystallization process and the suspension was allowed to stand for about 30 minutes. The crystals were filtered and washed with dry diethyl ether, then allowed to dry under aspirator vacuum. The crystals were dried in vacuo to give 4-amino-3-nitro-benzimidic acid ethyl ester hydrochloride (84.6 g) as off-white crystals.

Step 2

4-Amino-3-nitro-benzimidic acid ethyl ester hydrochloride (84.5 g, 344 mmol) was suspended in absolute ethanol (750 mL) and then cooled to 0° C. Ammonia was then passed through the solution for a period of 2 h. The flask was tightly sealed and allowed to warm up to room temperature over an 18 h period with stirring. The product was crystallized with diethyl ether and the resulting solid was filtered, washed and dried to give 4-amino-3-nitrobenzamidine monohydrochloride (70.7 g) as an off-white powder.

Step 3

A suspension of 4-amino-3-nitrobenzamidine monohydrochloride (15 g, 69 mmol) and Pearlman's catalyst [Pd(OH)$_2$, 1.0 g, 7.12 mmol) in methanol (200 mL) was shaken under hydrogen atmosphere 50 psi for 1.5 h. The suspension was filtered through Celite and the filtrate was added dropwise to anhydrous diethyl ether (400 mL) to precipitate 3,4-diaminobenzamidine monohydrochloride as a tan solid.

Reference C

Synthesis of N-tert-butyl 4-methoxy-5-(benzenesulfonamido)-3-boronic acid

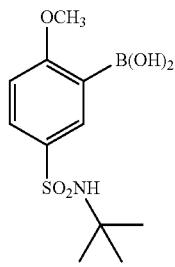

Step 1

A solution of 2-iodoanisole (221.2 g, 966 mmol) in dichloromethane (2.3 L) was cooled to 0° C. and chlorosulfonic acid (64.5 mL, 112.6 g, 966 mmol) was added dropwise with stirring over a 15-minute period. The reaction mixture was allowed to warm to 10° C. over 3 h. Nitrogen gas was passed over the solution and the outlet was bubbled through a solution of aqueous sodium hydroxide to scrub the gaseous hydrogen chloride produced in the reaction. An aliquot of the reaction was analyzed by HPLC, which showed that 2-iodoanisole had been consumed. The reaction mixture was treated with phosphorus pentachloride (217.8 g, 1.045 mol) and stirred at room temperature for 2 h. The reaction mixture was concentrated in vacuo to remove most of the volatile components then further concentrated at a bath temperature of 100° C. to remove POCl$_3$ produced in the reaction. The resulting oily residue was dissolved in CH$_2$Cl$_2$ (2.8 L) and this solution was stirred with water (3 L) while solid sodium bicarbonate was added to maintain the pH around 7. The layers were separated and the organic phase was cooled to 0° C., then tert-butylamine (230 mL, 160 g) was added at such a rate to maintain the internal temperature ≦10° C. The reaction mixture was allowed to warm up to ambient temperature overnight, then washed with 5% sodium hydroxide. The organic phase was concentrated in vacuo to give N-tert-butyl 3-iodo-4-methoxybenzenesulfonamide (340 g) as an off-white solid.

Step 2

N-tert-Butyl 3-iodo-4-methoxybenzenesulfonamide (335 g, 907 mmol) was dissolved in dichloromethane (3 L) and the resulting solution was cooled to an internal temperature of −20° C. The solution was treated with a 3.0 M solution of methylmagnesium bromide in diethyl ether (308 mL, 925 mmol) dropwise over 0.5 h to maintain the internal temperature of the flask at −20±5° C. The reaction mixture was allowed to stir at −20±5° C. for 2.5 h then a 2.13 M solution of isopropylmagnesium bromide in diethyl ether (511 mL, 1.09 mol) was added at about −35° C. The resulting solution was allowed to stir at −35±5° C. for 1.5 h. The reaction mixture was warmed to 0° C. and additional isopropylmagnesium bromide in diethyl ether (86.0 mL, 183 mmol) was added. The reaction mixture was stirred for 2 h at 0° C., then an additional aliquot of isopropylmagnesium bromide in diethyl ether (25.0 mL; 53.3 mmol) was added. The reaction mixture was treated with trimethylborate (320 mL; 2.90 mol) in THF (175 mL) in one portion, resulting in a temperature increase to 27° C. The reaction mixture was stirred at this temperature for 4 h, then poured into water (1.3 L) and 85% phosphoric acid was added until the solution was pH 2. The layers were separated and the organic phase was washed with 1.5 N aqueous NaOH (2 L), followed by 1% aqueous NaOH (2 L). The combined aqueous phases were acidified with phosphoric acid to pH 2 and the resulting acidic solution was extracted with 9:1 dichloromethane/THF solution (2 L followed by 1 L). The organic phase was dried (Na$_2$SO$_4$), filtered and concentrated in vacuo to give about 250 g of a white solid which was dissolved in ethanol (1 L). The solution was diluted with water to give a total volume of 4 L and the resulting solution was stirred at room temperature overnight. The resulting crystalline solid was filtered and dried under high vacuum overnight to afford N-tert-butyl 4-methoxy-5-(benzenesulfonamido)-3-boronic acid (221 g) as a white solid, which was a dihydrate (approximately). The filtrate was extracted with a 9:1 solution of dichloromethane/THF and the extract evaporated. The crude solid (23 g) was recrystallized from a 3:1 solution of water/ethanol (500 mL) to yield an additional 19 g of product as a white solid.

Reference D

Synthesis of methyl (5'-N-tert-butylsulfamoyl-5-formyl-2'-methoxy-6-methoxyethoxymethoxybiphenyl-3-yl)acetate

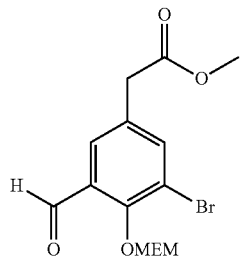

Step 1

To a 5-L round-bottom flask was added methyl (3-bromo-5-formyl-4-hydroxy-phenyl)acetate (210 g, 769 mmol, prepared in Reference A above), dichloromethane (2 L), and N,N-diisopropylethylamine (161 mL, 119 g, 923 mmol). A solution of 2-methoxyethoxy-methyl chloride (MEM chloride, obtained from TCI America; 106 mL; 923 mmol) in dichloromethane (500 mL) was added dropwise via an addition funnel over 2 h. The reaction was allowed to stir at ambient temperature for overnight, after which time HPLC analysis showed that the reaction was complete. The reaction mixture was diluted with 0.5 N aqueous HCl (1 L) and the solution was allowed to stir at ambient temperature for 0.25 h, then the layers were separated. The organic layer was washed with additional 0.5 N aqueous HCl, followed by saturated aqueous sodium chloride (1 L). The organic layer was concentrated under vacuum to give an oil, which later solidified upon standing. The solid could be crystallized from ethyl acetate and hexane to yield methyl[3-bromo-5-formyl-4-(2-methoxyethoxymethoxy)phenyl]-acetate (237 g) as a colorless solid.

Step 2

To a 12-L round bottom flask with a mechanical stirrer, heating mantle, and a reflux condenser was added methyl[3-bromo-5-formyl-4-(2-methoxyethoxymethoxy)-phenyl]acetate (215 g, 595 mmol), N-tert-butyl 4-methoxy-5-(benzenesulfonamido)-3-boronic acid (184.5 g, 643 mmol), N,N-diisopropylamine (275 mL, 1.79 mol), and THF (4 L). The solution was stirred, degassed under vacuum and placed under a nitrogen atmosphere. PdCl$_2$(dppf).dichloromethane complex (4.86 g, 5.95 mmol) was then added in one portion and the solution was heated to 70° C. for 16 h. The reaction mixture was allowed to cool to room temperature and it was then concentrated to remove most of the THF (3.5 L). The residue was diluted with ethyl acetate (4 L) and then washed with a 5% solution of potassium carbonate in water (3.0 L), followed by brine (2.0 L). DARCO-60 charcoal (8 g) was added to the organic phase and the resulting suspension was stirred at room temperature for 4 h. The solution was then dried over of sodium sulfate (200 g), the organic layer was then filtered through a fritted filter that was covered in layers of Celite (300 g), silica gel (300 g), and Celite (300 g). The filter cake was washed with a solution of 95:5 dichloromethane/methanol (1 L) and the resulting solution was concentrated in vacuo to give crude methyl (5'-N-tert-butylsulfamoyl-5-formyl-2'-methoxy-6-methoxyethoxymethoxy-biphenyl-3-yl)acetate as an oil, contaminated with methanol (~12 g) which was taken onto the next step without additional purification.

Reference E

Synthesis of 4-benzyloxy-N-tert-butyl-3-boronic acid-benzenesulfonamide

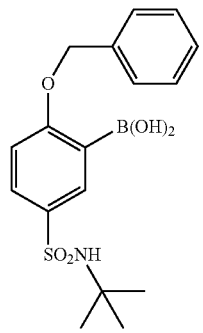

Method A

Step 1

To a 1 L round bottom flask was added 2-iodophenol (50 g) and nitromethane (250 mL) and the reaction mixture was cooled to 0° C. Fuming sulfuric acid (42 mL, 30% SO$_3$) was added dropwise and the reaction mixture was allowed to warm to room temperature. After 2 h, the reaction was complete and it was poured into water (400 mL) and washed with ethyl acetate (200 mL). The organic layer was then back extracted with water (300 mL) and concentrated to oil and combined with the original aqueous layer. The aqueous layer was then neutralized with 5 M aqueous sodium hydroxide (300 mL) and transferred to a 2 L round bottom flask. Sodium hydroxide pellet (11 g), ethanol (150 mL), and benzyl bromide (50 mL) were then added and the reaction mixture was heated to an oil bath temperature of 82° C. and stirred for 16 h. After the reaction was complete, ethanol was removed by vacuum distillation which caused the product to precipitate out of solution. The product was then filtered and dried under high vacuum to give 4-benzyloxy-3-iodo-benzenesulfonic acid (61 g, 70% yield).

Step 2

To a 2 L round bottom flask was added 4-benzyloxy-3-iodo-benzenesulfonic acid (49.87 g) and dichloromethane (1000 mL). The suspension was stirred and phosphorous pentachloride (53 g) was added causing the reaction to became a solution. After heating the reaction mixture at 40° C. for 1 h, aqueous sodium hydroxide (400 mL of 20%) was then slowly added and stirring was continued until the aqueous was pH 7. The organic layer was separated and stirred with 50% aqueous saturated sodium bicarbonate (125 mL) for 30 minutes (pH 10). The organic layer was separated, dried with anhydrous sodium sulfate, decanted to a 2 L round bottom flask and tert-butylamine (34 mL) was added. After 16 h, the reaction mixture was basified to pH 13-14 with 5% aqueous sodium hydroxide. The organic layer was separated and concentrated to a solid which was then slurried at 50° C. in isopropyl acetate, cooled, and filtered to give 4-benzyloxy-N-tert-butyl-3-iodo-benzenesulfonamide (46 g, 80% yield) in two crops.

Step 3

To a 1 L round bottom flask was added 4-benzyloxy-N-tert-butyl-3-iodo-benzenesulfonamide (32 g) and dichloromethane (320 mL) and the reaction mixture was stirred and cooled to −20 to −25° C. Methyl magnesium bromide (24.4 mL, 3 M in ether) was added dropwise. The reaction mixture was stirred for 2 h and then cooled to −35 to −40° C. Isopropyl magnesium bromide (54 mL of 2.13 M in ether) was added dropwise. Tetrahydrofuran (17 mL) and trimethyl borate (6 mL) were then added precipitating a white solid and raising the internal temperature of the reaction mixture to 0° C. The reaction mixture was allowed to warm to room temperature and after 12 h phosphoric acid (250 mL of 1M in 500 mL of water) was added. The organic layer was separated and basified with 2.5% aqueous sodium hydroxide (500 mL) causing some of the product to precipitate. The aqueous layer along with some of the precipitated solids was then acidified with concentrated phosphoric acid to a pH of 2 and extracted with 10% tetrahydrofuran in dichloromethane. The solids were carried on with the organic which was then concentrated to give a white solid that was then slurried in 1 L of water for 30 minutes. The solid was filtered and dried under high vacuum to give 4-benzyloxy-N-tert-butyl-3-boronic acid-benzenesulfonamide (23 g, 88% yield).

Method B: Alternate Synthesis of the Title Compound

Step 1

A 3-neck, 3 L-round-bottom flask was equipped with an over-head stirrer, thermometer, $N_2$ line, 250 mL pressure-equalizing dropping funnel, and gas-exit scrubber to a NaOH solution. The flask was flushed with $N_2$ and charged with 2-iodophenol (Alfa Aesar; 201.95, 0.918 mol) and dry dichloromethane (920 mL). A gentle stream of $N_2$ was established through the reaction head-space, the reaction vessel then immersed in a brine-ice bath and cooled to −5° C. The dropping funnel was charged with dry dichloromethane (175 mL), then chlorosulfonic acid (Aldrich; 106.96 g, 0.918 mol, 1.00 eq.), and the resulting mixture was stirred with a Teflon rod. The dilute solution of chlorosulfonic acid was then added dropwise to the reaction mixture over a period of approx. 90 mins. A thick pink slurry formed during the addition. Thirty minutes after complete addition, the ice bath was removed and the reaction mixture was allowed to stir at ambient temperature. After 2 h, the reaction vessel was immersed in a cold-water bath and water (500 mL) was added to the reaction mixture over a few minutes. The resulting mixture was stirred vigorously until it was biphasic/homogenous upon settling. The mixture was transferred to a separating funnel along with water and was extracted with dichloromethane. The aqueous layer containing 4-hydroxy-3-iodo-benzenesulfonic acid was transferred back to the original reaction vessel for the next step.

Step 2

Sodium hydroxide (pellets, 110 g, 2.75 mol, 3.00 eq) was added portionwise to the vigorously stirring aqueous solution of the 4-hydroxy-3-iodo-benzenesulfonic acid. After addition was complete, 10-15 min., isopropyl alcohol (150 mL) was added to the resulting white suspension. The dropping-funnel was charged with benzyl bromide (Aldrich; 164.9 g, 0.964 mol, 1.05 eq.) and added to the reaction mixture over a period of approx. 5 mins. and the reaction mixture was heated to $80° \leq T_{int} \leq 84°$ C. After approx. 25 min. it was determined that the reaction was not proceeding further and therefore additional sodium hydroxide (3.67 g, 91.8 mmol, 0.1 eq.) and then benzyl bromide (15.7 g, 91.8 mmol, 0.1 eq.) were added to the reaction mixture to give a homogenous solution. After 70 min. from the original benzyl bromide addition, the heating was stopped and the reaction was allowed to cool slowly in the oil-bath with stirring. At 7.5 h, the reaction mixture appeared as a suspension of fine-reflective precipitate in brown liquid. The reaction mixture was acidified with 3:1 water-sulfuric acid from about pH 13 to between pH 7.5 and 8 (approx. 70 mL is required). The reaction mixture was then cooled gradually to about 5° C. and stirred at that temperature for ~1 h. The waxy white plaques were collected by filtration, washed with dichloromethane and dried under high vacuum (lyophilizer, 100-200 mTorr) for ~24 h to give sodium 4-benzyloxy-3-iodo-benzenesulfonate as a brilliant white, crystalline solid, (267.7 g, 71%).

Step 3

A 3-neck, 3 L, round-bottom flask was equipped with an over-head stirrer, reflux condenser (with gas exit to NaOH scrub solution), and a pressure-equalizing dropping-funnel with $N_2$ line. The flask was flushed with $N_2$, charged with sodium 4-benzyloxy-3-iodo-benzenesulfonate (234 g, 0.568 mol), dichloromethane (1.15 L), and catalytic amount of dimethylformamide (910 mg, 11.7 mmol, 2.1 mol%). The white suspension was stirred under a gentle stream of nitrogen and heated in an oil-bath set between 40 and 45° C. Oxalyl chloride (90.1 g, 0.710 mol, 1.25 eq) was then added over 3-5 min. After 2.5 h, the reaction was allowed to cool to 25° C. in a cold-water bath and then quenched drop-wise with water (60 mL) over approx. 5 min. A further portion of water (450 mL) was added in a single portion and the reaction mixture stirred vigorously for 5 to 10 min. The organic layer was separated and washed with water until the aqueous pH had increased to pH 4 to 5). The resulting dichloromethane solution of 4-benzyloxy-3-iodo-benzenesulfonyl chloride was used in the next step.

Step 4

A 3-neck, 3 L, round-bottom flask was equipped with an over-head stirrer, thermometer, and a pressure-equalizing dropping-funnel was charged with the solution of 4-benzyloxy-3-iodo-benzenesulfonyl chloride. The flask immersed in a cold water bath ($T_{int}$=22° C.) and tert-butylamine (90.1 g, 0.710 mol, 2.1 eq) was added drop-wise ($T_{int}$ no change). The resulting reaction mixture was stirred overnight at the ambient water-bath temperature. After 17 h, the reaction mixture was worked-up and the organic layer was separated and concentrated to approx. ⅓ (~500 mL) of its original volume at which point the product started to precipitate. The reaction mixture was warmed to 35-40° C. at atmospheric pressure till the solids had re-dissolved. The solution was then allowed to cool, with gentle stirring, to room temperature. Within 2 days a white precipitate had formed. The suspension was stirred vigorously while hexane (1.5 L) was slowly added, then stirred overnight, and then cooled in an ice-bath for 1-2 h The precipitate was collected by filtration and washed with hexane, dried, first under suction to give 4-benzyloxy-N-tert-butyl-3-iodo-benzenesulfonamide (238, 94%).

Step 5

A 3-neck, 2 L-round-bottom flask was equipped with an over-head stirrer, thermometer, pressure-equalizing dropping-funnel, and an $N_2$ line. The flask was flushed with $N_2$ and then charged with 4-benzyloxy-N-tert-butyl-3-iodo-benzenesulfonamide (198.6 g, 0.446 mol) and dichloromethane (600 mL). The white suspension was stirred under a gentle stream of $N_2$ and cooled in an ice-water bath (0° C. $\leq T_{int} \leq$ 5° C.). The dropping-funnel was charged with methyl magnesium bromide (Aldrich; 3.0 M in diethyl ether, 167 g, ~171 mL, 0.513 mol, 1.15 eq), which was added dropwise to the suspension at such a rate so as to maintain $T_{int} \leq$ 5° C. (addition of salt to the cool-bath was necessary) to give a colorless-homogenous mixture within ~⅓ addition. After the addition was completer, the dropping-funnel was charged with isopropylmagnesium bromide (Boulder Scientific; 2.13 M in diethyl ether; 250 mL, 0.533 mol, 1.2 eq), which was added dropwise to the reaction mixture at such a rate so as to maintain $T_{int}$<5° C. After the addition was complete, the reaction mixture was stirred for 15-20 min. The dropping-funnel was removed and replaced with a septa and cannula, and the reaction mixture was transferred over 2 h to a 3-necked, 3-L round bottom flask containing a solution trimethyl borate (106.6 g, 1.03 mol, 2.30 eq) and tetrahydrofuran (600 mL) and maintained under nitrogen atomosphere at ($T_{int}$<5° C.) utilizing an ice-water bath. After the addition was complete, the solution was allowed to stir at <5° C. for 30 min. and then transferred to a separatory funnel and washed with an equal volume of a 2:1 (water:phosphoric acid) solution. The organic layer was dried over sodium sulfate. Ethyl acetate was added to the solution and the combined organic layer was concentrated to give 4-benzyloxy-N-tert-butyl-3-boronic acid-benzenesulfonamide (129 g, 80%).

Reference F

Synthesis of (4-benzyloxy-3-bromo-5-formyl-phenyl)acetic acid methyl ester

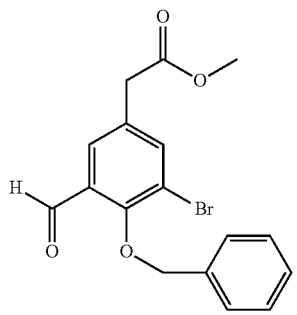 [SMILES: COC(=O)Cc1cc(Br)c(OCc2ccccc2)c(C=O)c1]

To a 250 mL round-bottomed flask with a teflon stir bar and a reflux condensor were added methyl (3-bromo-5-formyl-4-hydroxyphenyl)acetate (23.3 g, 85.3 mmol, prepared as described in Reference A above), dichloromethane (100 mL), benzyl bromide (15.32 g, 10.64 mL, 89.59mmol), and N-ethyldiisopropylamine (11.6 g, 15.6 mL, 89.5 mmol). The reaction mixture was heated to reflux for 14 h and then allowed to cool to room temperature. Dichloromethane (100 mL) was added and the organic layer was separated and washed with 200 mL of a 3% solution of NaOH in water. The organic layer was concentrated to give (4-benzyloxy-3-bromo-5-formyl-phenyl)acetic acid methyl ester (30.65 g) as oil.

Example 1

Synthesis of (S)-2-{2-[5-(5-carbamimidoyl-1H-benzimidazol-2-yl)-6,2'-dihydroxy-5'-sulfamoylbiphenyl-3-yl]acetylamino}succinic acid

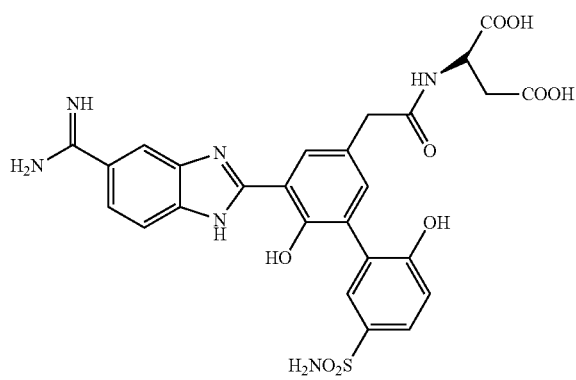

Method A
Step 1

To a 12-L round bottom flask with stir bar was added methyl (5'-N-tert-butylsulfamoyl-5-formyl-2'-methoxy-6-methoxyethoxymethoxybiphenyl-3-yl)acetate (324.3 g), methanol (5.2 L), followed by addition of concentrated aqueous HCl (0.29 L) dropwise to maintain the internal temperature of the flask below 25° C. The reaction mixture was allowed to stir at room temperature overnight by which time the product had precipitated from solution. The reaction mixture was cooled to −20° C., and filtered and the resulting solid was then washed with an additional portion of methanol (750 mL) that had been previously cooled to −25° C. The off-white solid was dried in a vacuum chamber to give methyl [5'-N-tert-butylsulfamoyl-5-formyl-6-hydroxy-2'-methoxy)biphenyl-3-yl]acetate (205 g).

Step 2

To a 12-L round bottom flask with a mechanical stirrer and heating mantle was added methyl[5'-N-tert-butylsulfamoyl-5-formyl-6-hydroxy-2'-methoxy)biphenyl-3-yl]acetate (200.8 g, 461 mmol), isopropanol (2.3 L) and a solution of sodium metabisulfite (106.4 g, 553 mmol) dissolved in water (0.21 L). The resulting suspension was heated to 60° C. for 2.5 h. 3,4-Diaminobenzamidine monohydrochloride (115.2 g, 617 mmol) was added and a stream of air was then allowed to circulate through the flask. The solution turned orange and became homogeneous after 0.25 h. After 1 h, the reaction was shown to be 70% complete by HPLC analysis, but required a reaction time of about 18 h to go to completion resulting in the precipitation of the product. The reaction mixture was cooled to room temperature and filtered. The solid was washed with isopropanol (1 L) and dried in a vacuum chamber to give methyl[5'-N-tert-butylsulfamoyl-5-(5-carbamimidoyl-1H-benzimidazol-2-yl)-6-hydroxy-2'-methoxybiphenyl-3-yl]-acetate (264 g) as a mustard-colored solid.

Step 3

To a 3-L round bottom flask was added methyl [5'-N-tert-butylsulfamoyl-5-(5-carbamimidoyl-1H-benzimidazol-2-yl)-6-hydroxy-2'-methoxybiphenyl-3-yl]-acetate (49.9 g, 82.9 mmol) and trifluoroacetic acid (770 mL). The reaction mixture was allowed to stir at room temperature for 1.5 h then concentrated in vacuo. Methanol (1 L) was added to the gel-like residue and the solution was concentrated again then dried under high vacuum overnight. The dry, solid product was transferred to a 3 L 3-neck round bottom flask fitted with a Dean-Stark trap, a stirring shaft and a nitrogen inlet. The flask was flushed with nitrogen then pyridine hydrochloride (412 g, 3.57 mol) and toluene (100 mL) were added. The reaction mixture was heated under reflux to remove residual water from the pyridine salt and solvent. The solution was heated to 150° C. to melt the pyridine hydrochloride after which the temperature was increased to 180° C. over 0.5 h. After 1.5 h, the solution was cooled under a positive pressure of nitrogen until it solidified and reached room temperature. Water (3 L) was added and the solution was allowed to stir at room temperature overnight. The reaction mixture was filtered and the solid was washed with water (200 mL) and isopropanol (100 mL). The solid was dried in a vacuum chamber overnight to yield [5-(5-carbamimidoyl-1H-benzimidazol-2-yl)-6,2'-dihydroxy-5'-sulfamoyl-biphenyl-3-yl]-acetic acid (38.15g) which was contaminated with about 4% sulfonic acid.

Alternative Synthesis of [5-(5-carbamimidoyl-1H-benzimidazol-2-yl)-6,2'-dihydroxy-5'-sulfamoyl-biphenyl-3-yl]-acetic acid Pyridine (69.0 g, 70.4 mL, 0.87 mol) in anhydrous ether (200 mL) was treated with 4 M HCl in dioxane (250 mL, 1.0 mol) until precipitation of the salt was complete. Excess solvent was removed by evaporation and toluene (500 mL) was added. The reaction mixture was refluxed for 2-3 h with a Dean-Stark trap. After cooling, toluene was evaporated as completely as possible and the flask containing the solid pyridine.HCl was immersed in an oil bath heated at 180-185° C. and allowed to melt. The melted pyridine.HCl was heated at 180-185° C. for 30-60 minutes while connected to a drying tube. Next, the melted salt was treated in one portion with moderate stirring with methyl[5-(5-carbamimidoyl-1H-benzimidazol-2-yl)-6-hydroxy-2'-methoxy-5'-sulfamoyl-biphenyl-3-yl]acetate (25.0 g, 29.4 mmol) (obtained from the TFA treatment of methyl[5'-N-tert-butylsulfamoyl-5-(5-carbamimidoyl-1H-benzimidazol-2-yl)-6-hydroxy-2'-methoxybiphenyl-3-yl]-acetate). The hot solution was heated with stirring for 60-90 minutes until the reaction was complete by HPLC analysis. After cooling, the solid mixture was dissolved in water (800 mL) and stirred overnight. The resulting solid was filtered and dried in vacuo to give [5-(5-carbamimidoyl-1H-benzimidazol-2-yl)-6,2'-dihydroxy-5'-sulfamoyl-biphenyl-3-yl]-acetic acid (13-14 g) containing ~1-2% of sulfonic acid impurities.

Step 4

To a magnetically stirred solution of [5-(5-carbamimidoyl-1H-benzimidazol-2-yl)-6,2'-dihydroxy-5'-sulfamoyl-biphenyl-3-yl]-acetic acid (14.0 g, 27.1 mmol) in N,N-dimethylacetamide (125 mL) at 0° C. was added N-methylmorpholine (5.95 mL, 54.2 mmol), EDC (5.71 g, 29.8 mmol) and HOBt (4.00 g, 29.8 mmol). The reaction mixture was allowed to stir at 0° C. for 0.5 h. A solution of H-Asp-(OBn)-OBn.HCl (10.4 g, 29.8 mmol) in DMA (25 mL) was added to the reaction mixture and the resulting solution was stirred at ambient temperature for 12 h. The solution was concentrated in vacuo under high vacuum, maintaining the water bath temperature below 50° C. to remove most of the DMA. The residual oil was suspended in acetonitrile (150 mL) and the reaction mixture was allowed to stir at ambient temperature for 0.5 h, after which time the product had precipitated from solution. The solid was removed by filtration and it was washed with acetonitrile. The solid was suspended in a saturated aqueous solution of sodium bicarbonate (150 mL), stirred at room temperature for 0.5 h, and then filtered. The resulting solid was then suspended in a 10 mM aqueous HCl solution (150 mL) and allowed to stir at room temperature for 0.5 h. The suspension was filtered and dried to give dibenzyl(S)-2-{2-[5-(5-carbamimidoyl-1H-benzimidazol-2-yl)-6,2'-dihydroxy-5'-sulfamoylbiphenyl-3-yl]acetylamino}succinate (18 g) that was 80-90% pure by analytical HPLC. The crude dibenzyl(S)-2-{2-[5-(5-carbamimidoyl-1H-benzimidazol-2-yl)-6,2'-dihydroxy-5'-sulfamoylbiphenyl-3-yl] acetylamino}succinate was taken directly onto the next step without additional purification.

Step 5

Crude dibenzyl(S)-2-{2-[5-(5-carbamimidoyl-1H-benzimidazol-2-yl)-6,2'-dihydroxy-5'-sulfamoylbiphenyl-3-yl] acetylamino}succinate (18 g) was dissolved in a 1:1 mixture of acetic acid and water (800 mL), assisted by sonication. To this solution was added palladium hydroxide on carbon (Pearlman's catalyst, 20 wt % Pd on a dry weight basis, containing 50% water by weight; 7.0 g). The reaction mixture was pressurized to 30 psi with hydrogen and the suspension was shaken on a Parr apparatus for 10 h. The catalyst was removed by filtration and the solvent was removed in vacuo. Crude (S)-2-{2-[5-(5-carbamimidoyl-1H-benzimidazol-2-yl)-6,2'-dihydroxy-5'-sulfamoylbiphenyl-3-yl] acetylamino}succinic acid was purified by preparative reverse-phase HPLC to give (S)-2-{2-[5-(5-carbamimidoyl-1H-benzimidazol-2-yl)-6,2'-dihydroxy-5'-sulfamoylbiphenyl-3-yl]acetylamino}succinic acid (7.2 g).

Method B: Alternate Synthesis of [5-(5-carbamimidoyl-1H-benzimidazol-2-yl)-6,2'-dihydroxy-5'-sulfamoyl-biphenyl-3-yl]-acetic acid Step 1

To a 1 L round bottom flask with magnetic stir bar and a nitrogen reflux condensor was added crude (4-benzyloxy-3-bromo-5-formyl-phenyl)acetic acid methyl ester (19.36 g, 53.31 mmol), tetrahydrofuran (400 mL), diisopropyl amine (16.7 g, 23.2 mL, 165.1 mmol) and 4-benzyloxy-N-tert-butyl-3-boronic acid-benzenesulfonamide (21.74 g, 59.7 mmol). The reaction mixture was placed under a nitrogen atmosphere and dichloro[1,1'-bis(diphenylphosphino)ferrocene]palladium(II)dichloromethane adduct (0.68 g, 0.832 mmol) was added. The reaction mixture was heated to reflux for 16 h at which time it was complete by HPLC. The solution was concentrated to a solid and methyl tert-butyl ether (500 ml) was added to dissolve the solid. The solution was washed twice with 3% cold aqueous sodium hydroxide solution (500 mL). The organic layer was filtered through a plug of Celite (200 g) and silica gel (100 g). The Celite was washed with a 1:1 mixture of methyl tert-butyl ether and ethyl acetate (400 mL). The filterate was concentrated to give (6,2'-bisbenzyloxy-5'-N-tert-butylsulfamoyl-5-formyl-biphenyl-3-yl)-acetic acid methyl ester (32 g) as oil, which was taken directly onto the next step without additional purification.

Step 2

To a 250 mL round-bottom flask with stir bar was added crude (6,2'-bisbenzyloxy-5'-N-tert-butylsulfamoyl-5-formyl-biphenyl-3-yl)-acetic acid methyl ester (5.00 g, 8.31 mmol), methanol (50 mL) and water (5 mL). The reaction mixture was warmed to 60° C. and sodium metabisulfite (1.58 g, 8.31 mmol) was added, and the reaction mixture was allowed to stir at 60° C. for 2.5 h. 3,4-Diaminobenzamidine hydrochloride (1.80 g, 9.64 mmol) was added in one portion and the reaction mixture was heated at 60° C. overnight. The reaction mixture was cooled to room temperature and 250 mL of a (3:1) isopropyl acetate:isopropanol solution was added followed by addition of water (50 mL). The organic layer was separated, filtered through Celite, dried over sodium sulfate, and concentrated to give [6,2'-bisbenzyloxy-5'-N-tert-butyl-sulfamoyl-5-(5-carbamimidoyl-1H-benzimidazolyl-2-yl)-biphenyl-3-yl]-acetic acid methyl ester hydrochloride (5.8 g, 91%) as a light brown solid.

Alternative Method to Step 2

To a 500 mL round bottom flask with stir bar and a reflux condensor was added crude (6,2'-bisbenzyloxy-5'-N-tert-butylsulfamoyl-5-formyl-biphenyl-3-yl)-acetic acid methyl ester (20 g, 33.23 mmol) and 3,4-diaminobenzamidine (7.44 g, 39.88 mmol), PdCl$_2$(MeCN)$_2$ (100 mg, Strem Chemicals), followed by addition of a 9:1 mixture of isopropanol:water (200 mL) and a solution of sodium metabisulfite (6.3 g, 33.2 mmol) in water (30 mL). The reaction mixture was heated to reflux with an oil bath and the top of the reflux condensor was left open to the air. The solution was heated to reflux overnight, at which time it was complete by HPLC. To this solution was added Darco (5 g) and the solution was filtered hot through celite (100 g). The celite was washed with isopropanol (100 mL) and the resulting solution was extracted with ethyl acetate (300 mL) and brine (70 mL). The organic layer was concentrated to give [6,2'-bisbenzyloxy-5'-N-tert-butyl-sulfamoyl-5-(5-carbamimidoyl-1H-benzimidazolyl-2-yl)biphenyl-3-yl]-acetic acid methyl ester hydrochloride as an amorphous solid that was carried onto the next step without any additional purification.

Step 3

To a 50 mL round bottom flask was added [6,2'-bisbenzyloxy-5'-N-tert-butylsulfamoyl-5-(5-carbamimidoyl-1H-benzimidazolyl-2-yl)-biphenyl-3-yl]-acetic acid methyl ester hydrochloride (0.500 g, 0.651 mmol) and glacial acetic acid (2.5 mL). 12 N HCl (aq) (2.5 mL) was added and the reaction mixture was heated to 50° C. After 14 h, the reaction mixture was added to water (100 mL) and the solution was concentrated to 5 mL in vacuo to give a precipitate. The precipitate was removed by filtration to give [5-(5-carbamimidoyl-1H-benzimidazol-2-yl)-6,2'-dihydroxy-5'-sulfamoyl-biphenyl-3-yl]-acetic acid (365 mg) which contained water and 2.8 eq. of HCl (93%) which was then be converted to the title compound as described above.

Alternative Method to Step 3

To a 1 L round bottom flask was added crude [6,2'-bisbenzyloxy-5'-N-tert-butylsulfamoyl-5-(5-carbamimidoyl-1H-benzimidazolyl-2-yl)-biphenyl-3-yl]-acetic acid methyl ester hydrochloride (22.0 g, 28.65 mmol) and glacial acetic acid (400 mL). To this solution was added 12 N HCl (aq) (400 mL) and the reaction mixture was allowed to heat to 55° C. and the reaction was >95% complete by HPLC after 14 h. To this solution was added Darco (2 g). The solution was allowed to stir at 55° C. for an additional hour and the solution was filtered through celite to remove the charcoal. The solution was concentrated under reduced pressure to a solid which was treated with 1N HCl (600 mL) and acetonitrile (200 mL). Upon heating the solid dissolved and at that time Darco (6 g) was added. The solution was allowed to stir at 70° C. for 1 h and it was filtered hot through celite. The solution was allowed to cool to room temperature and the precipitate was filtered to give [5-(5-carbamimidoyl-1H-benzimidazol-2-yl)-6,2'-dihydroxy-5'-sulfamoyl-biphenyl-3-yl]-acetic acid (9.85 g, 66%).

Example 2

Synthesis of (S)-2-{2-[5-(5-carbamimidoyl-1H-benzimidazol-2-yl)-6,2'-dihydroxy-5'-sulfamoylbiphenyl-3-yl]acetylamino}succinic acid zwitterion Purified lyophilized (S)-2-{2-[5-(5-carbamimidoyl-1H-benzimidazol-2-yl)-6,2'-dihydroxy-5'-sulfamoylbiphenyl-3-yl]acetylamino}succinic acid (11 g) powder was suspended in 130 mL of 2 M HCl (aqueous) and warmed to 60° C. THF (80 mL) was added to this suspension and stirred at that temperature until the compound was completely dissolved (pH of the the solution was kept around ~2.0). This solution was filtered while hot and stirred slowly at room temperature for 24 h after adding seed crystals. Crystalline material (5.2 g) was filtered at room temperature, was washed with water until washings were neutral (pH 7). Elemental analysis and chloride content analysis revealed absence of any chloride counter ion, indicating that the material is zwitter-ionic.

$^1$H NMR (DMSO-d$_6$): 9.21 (2 H, br s), 8.87 (2 H, br s), 8.21 (1 H, d, J=7.8 Hz), 8.0 (2 H, d, J=7.2 Hz), 7.79 (1 H, d, J=7.8 Hz), 7.73 (J=1.5 Hz, 1 H, d), 7.6 (J=8.6, 1.5 Hz, dd, 1 H), 7.5 (1 H, dd, J=8.5 and 2.5 Hz), 7.2 (1 H, d, J=2.3 Hz), 4.3 (1 H, J=2.3, 5.3 Hz, dd), 3.5 (2 H, s), 2.6 (1 H, dd, J=16 and 7.3 Hz), 2.44 (1 H, dd, J=5.3 Hz).

Biological Examples

Example 1

In Vitro Factor VIIa Inhibitor Assay

Mixtures of human Factor VIIa (typically supplied at 7 nM) and test compound (present at varying concentrations) in assay medium (comprising: NaCl, 150 mM (pH 7.4); CaCl$_2$, 5 mM; Tween-20, 0.05% ; Dade Innovin tissue factor [Dade Behring, Newark, Del., USA]; EDTA, 1.5 mM; and dimethylsulfoxide, 10%) were incubated for 30 minutes at room temperature. Next, reactions were initiated with the addition of substrate [500 μM of CH$_3$SO$_2$-D-Cha-But-Arg-pNA (from Centerchem, Norwalk, Conn., USA)]. Hydrolysis of the chromogenic substrate was followed spectrophotometrically at 405 nm for five minutes. Initial velocity measurements calculated from the progress curves by a kinetic analysis program (Batch Ki; BioKin, Ltd., Pullman, Wash.) were used to determine apparent inhibition constants (apparent K$_i$'s).

Compounds of the invention tested by the above-described assay exhibited inhibition of Factor VIIa.

Example 2

In Vitro Factor Xa Inhibitor Assay

Mixtures of human Factor Xa (typically supplied at 3 nM) (from Haematologic Technologies, Essex Junction, Vt., USA) and test compound (varying concentrations) in assay medium (comprising: Tris, 50 mM (pH 7.4); NaCl, 150 mM; CaCl$_2$, 5 mM; Tween-20, 0.05%; EDTA, 1 mM; and dimethylsulfoxide, 10%) were incubated for 30 minutes at room temperature. Next, reactions were initiated with the addition of substrate [500 μM of CH$_3$CO$_2$-D-Cha-Gly-Arg-pNA (from Centerchem, Norwalk, Conn., USA]. Hydrolysis of the chromogenic substrate was followed spectrophotometrically at (405 nm) for five minutes. Apparent inhibition constants (apparent K$_i$'s) were calculated from the enzyme progress curves using standard mathematical models.

Compounds of the invention tested by the above-described assay exhibited inhibition of Factor Xa.

Example 3

Pharmacokinetic Assay

Rats with pre-implanted jugular vein catheters, which were filled with heparin/saline/PVP lock prior to shipment, were bought from Charles River. Three rats were selected for each study, weighed, and injected with test compound by tail vein injection. Any residual test compound was retained and stored at −70° C. for later analysis.

Blood samples (0.25 mL each) were collected from the indwelling catheters at specified times over 120 h. The catheters were flushed with physiological saline immediately after each collection and filled with heparinized saline after each 8, 24 and 48 h collection. In the event that a catheter failed, blood samples were collected via the retro-orbital sinus under isoflurane anesthesia at the appropriate time.

Blood samples were placed in 0.5 mL Microtainer® tubes (lithium heparin), shaken gently and stored on wet ice. The samples were centrifuged for 10 minutes at 2400 rpm in a refrigerated centrifuged. Plasma samples (0.1 mL) from each tube were transferred to 0.5 mL Unison polypropylene vials (Sun—500210) and stored below −70° C. for later analysis by LC/MS-MS.

Example 4

In vitro Clotting Assays . . . aPTT and PT

Coagulation assays, activated partial thromboplastin time (aPTT) and prothrombin time (PT) were carried out based on the procedure described in Hougie, C. *Hematology* (Williams, W. J., Beutler, B., Erslev, A. J., and Lichtman, M. A., Eds.), pp. 1766-1770 (1990), McGraw-Hill, New York.

Briefly, the assays were performed using normal human citrated plasma and were performed at 37° C. on a coagulometer (Electra 800) in accordance with the manufacturer's instructions (Medical Laboratory Automation—Pleasantville, N.Y.). The instrument was calibrated with plasma immediately prior to collecting clotting times for samples with inhibitors. The aPTT and PT doubling concentrations were calculated by fitting inhibitor dose response curves to a modified version of the Hill equation.

Pharmaceutical Composition Examples

The following are representative pharmaceutical formulations containing a compound of Formula I.

Tablet Formulation

The following ingredients are mixed intimately and pressed into single scored tablets.

| Ingredient | Quantity per tablet, mg |
| --- | --- |
| compound of this invention | 400 |
| cornstarch | 50 |
| croscarmellose sodium | 25 |
| lactose | 120 |
| magnesium stearate | 5 |

Capsule Formulation

The following ingredients are mixed intimately and loaded into a hard-shell gelatin capsule.

| Ingredient | Quantity per capsule, mg |
| --- | --- |
| compound of this invention | 200 |
| lactose, spray-dried | 148 |
| magnesium stearate | 2 |

Suspension Formulation

The following ingredients are mixed to form a suspension for oral administration.

| Ingredient | Amount |
| --- | --- |
| compound of this invention | 1.0 g |
| fumaric acid | 0.5 g |
| sodium chloride | 2.0 g |
| methyl paraben | 0.15 g |
| propyl paraben | 0.05 g |
| granulated sugar | 25.5 g |
| sorbitol (70% solution) | 12.85 g |
| Veegum K (Vanderbilt Co.) | 1.0 g |
| flavoring | 0.035 mL |
| colorings | 0.5 mg |
| distilled water | q.s. to 100 mL |

Injectable Formulation

The following ingredients are mixed to form an injectable formulation.

| Ingredient | Amount |
| --- | --- |
| compound of this invention | 1-2 g |
| sodium acetate buffer solution, | 0.4M 2.0 mL |
| HCl (1N) or NaOH (1N) | q.s. to suitable pH |
| water (distilled, sterile) | q.s. to 20 mL |

All of the above ingredients, except water, are combined and heated to 60-70° C. with stirring. A sufficient quantity of water at 60° C. is then added with vigorous stirring to emulsify the ingredients, and water then added q.s. to 100 g.

Suppository Formulation

A suppository of total weight 2.5 g is prepared by mixing the compound of the invention with Witepsol® H-15 (triglycerides of saturated vegetable fatty acid; Riches-Nelson, Inc., New York), and has the following composition:

| | |
| --- | --- |
| compound of the invention | 500 mg |
| Witepsol ® H-15 | balance |

Parenteral Formulation

| | |
| --- | --- |
| Compound (Ib) | 40 mg/mL |
| Hydroxypropyl-β-cyclodextrin | 200 mg/mL |
| Adjust pH with 1.0N sodium hydroxide to 7.4 | |

The foregoing invention has been described in some detail by way of illustration and example, for purposes of clarity and understanding. It will be obvious to one of skill in the art that changes and modifications may be practiced within the scope of the appended claims. Therefore, it is to be understood that the above description is intended to be illustrative and not restrictive. The scope of the invention should, therefore, be determined not with reference to the above description, but should instead be determined with reference to the following appended claims, along with the full scope of equivalents to which such claims are entitled.

We claim:
1. An intermediate of formula (II):

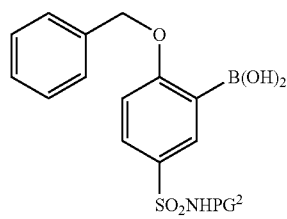

(II)

wherein $PG^2$ is a suitable amino-protecting group.

2. A method of preparing an intermediate of formula (II):

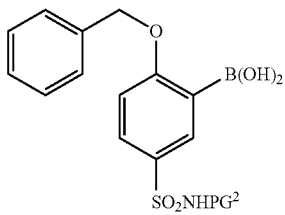

(II)

wherein $PG^2$ is a suitable amino-protecting group, comprising:

(i) reacting a compound of formula (III):

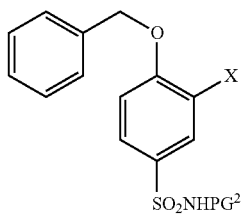

(III)

wherein $PG^2$ is a suitable amino-protecting group, and X is halo; with one equivalent of an organometallic agent of formula RLi or $RMgX^1$ where R is alkyl or aryl and $X^1$ is halo;

(ii) transmetallating the compound generated in Step (i) above with one equivalent of an organometallic agent of formula RLi or $RMgX^1$ where R is alkyl or aryl;

(iii) treating the compound generated in Step (ii) above with trialkylborate to generate a compound of formula (II).

3. The method of claim 2, wherein the organometallic reagent in step (i) is methyl magnesium bromide and the organometallic reagent in step (ii) is isopropyl magnesium bromide.

* * * * *